(12) United States Patent  
Tanaka

(10) Patent No.: US 7,316,767 B2  
(45) Date of Patent: Jan. 8, 2008

(54) GAS SENSING ELEMENT

(75) Inventor: Akio Tanaka, Gifu (JP)

(73) Assignee: Denso Corporation, Kariya, Aichi-pref. (JP)

( * ) Notice: Subject to any disclaimer, the term of this patent is extended or adjusted under 35 U.S.C. 154(b) by 716 days.

(21) Appl. No.: 10/652,555

(22) Filed: Sep. 2, 2003

(65) Prior Publication Data

US 2004/0069630 A1   Apr. 15, 2004

(30) Foreign Application Priority Data

Aug. 30, 2002 (JP) ............................ 2002-254068  
Oct. 31, 2002 (JP) ............................ 2002-318520

(51) Int. Cl.  
*G01N 27/407* (2006.01)

(52) U.S. Cl. ...................... 204/425; 204/427; 205/785; 73/23.31

(58) Field of Classification Search ................ 204/424, 204/425, 427; 205/781, 785; 73/23.31  
See application file for complete search history.

(56) References Cited

U.S. PATENT DOCUMENTS

| | | | |
|---|---|---|---|
| 4,814,059 A * | 3/1989 | Nishizawa et al. ......... | 204/406 |
| 4,909,922 A * | 3/1990 | Kato et al. ................. | 204/406 |
| 5,236,569 A | 8/1993 | Murase et al. | |
| 5,866,799 A | 2/1999 | Kato et al. | |
| 5,976,335 A * | 11/1999 | Kato et al. .................. | 204/425 |
| 6,270,638 B1 * | 8/2001 | Kaneko ....................... | 204/424 |
| 6,613,207 B1 * | 9/2003 | De La Prieta et al. ...... | 204/426 |
| 2002/0050455 A1 * | 5/2002 | Kurokawa et al. .......... | 204/431 |

FOREIGN PATENT DOCUMENTS

| | | |
|---|---|---|
| JP | S63-214663 | 9/1988 |
| JP | H03-167467 | 7/1991 |
| JP | 2885336 | 2/1999 |
| JP | 2000-180403 | 6/2000 |
| JP | 2000-180409 | 6/2000 |
| JP | 2001-041927 | 2/2001 |
| JP | 2001-254068 | 9/2001 |
| JP | 2002-521688 | 7/2002 |

OTHER PUBLICATIONS

Japanese Office Action dated Dec. 27, 2005.

* cited by examiner

*Primary Examiner*—Kaj K. Olsen  
(74) *Attorney, Agent, or Firm*—Nixon & Vanderhye P.C.

(57) ABSTRACT

Provided is a multilayer gas sensing element having a high measurement accuracy and less susceptible to a leakage current. The element comprises an oxygen pump cell for adjusting an oxygen concentration in a measured gas chamber, a sensor cell for detecting a specified gas concentration in the measured gas chamber, and a heater for heating the cells up to an activating temperature. The heater includes a heat generator for generating heat when energized, a heater terminal provided externally and a heater lead for making electrical connection therebetween. When the electrical resistance value of the heat generator is taken as RH and the electrical resistance value of the heater lead is taken as RL, these values are set to satisfy the relationship of $1.5 \leq RH/RL$.

5 Claims, 21 Drawing Sheets

(FRONT)

(BACK)

(FRONT)

(FRONT)

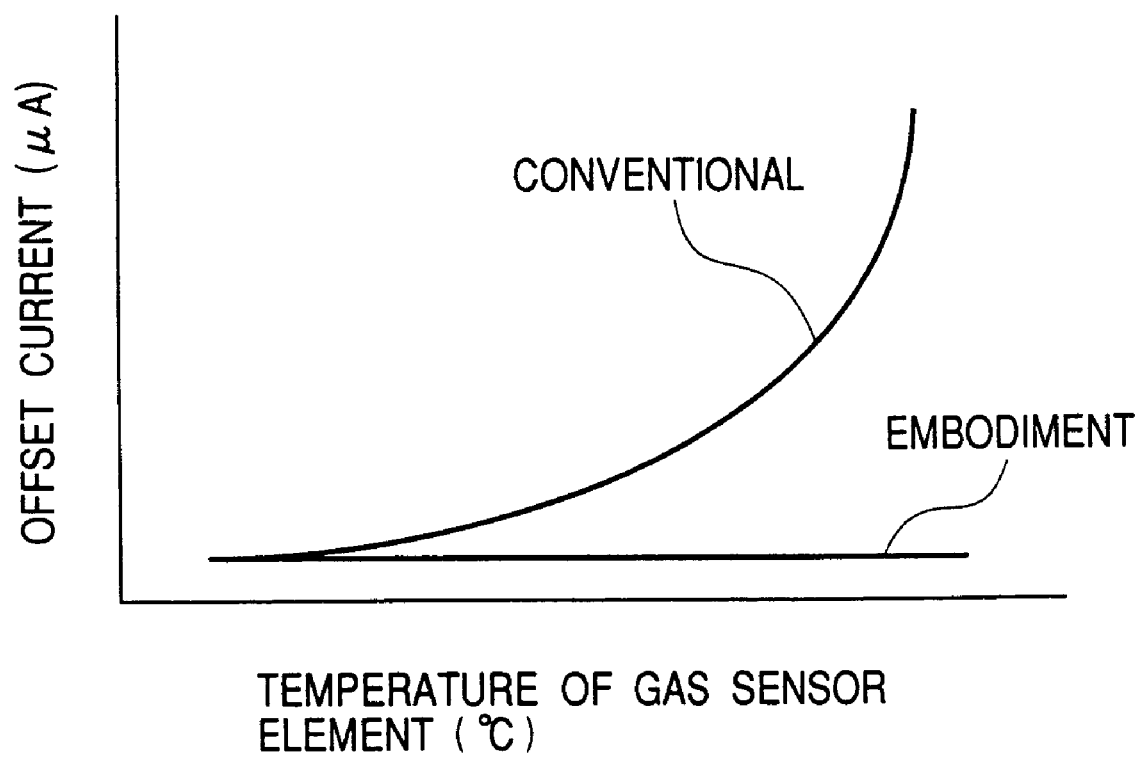

GAS SENSING ELEMENT

BACKGROUND OF THE INVENTION

1) Field of the Invention

The present invention relates to a multilayer gas sensing element applicable to an exhaust system of an internal combustion engine of a vehicle or the like, and employable for the purpose of the detection of NOx concentration or the like, and further to a gas sensing element to be built in a gas sensor for combustion control of an internal combustion engine of a vehicle and other applications.

2) Description of the Related Art

Exhaust gases emitted from internal combustion engines of vehicles and others create air contamination, which causes serious problems in the modern society, and the purification standard regulations regarding NOx and others in the exhaust gases, which form pollution substances, have taken on an intensity year by year.

Meanwhile, it is considered that, if a concentration of NOx in an exhaust gas is detected and the detection result is feedbacked to an engine combustion control monitor, a catalyst monitor or the like, the exhaust gas purification is more efficiently achievable. Such a situation requires a gas sensing element capable of accurately detecting the NOx concentration in the exhaust gas.

As a well-known conventional multilayer gas sensing element, there is an element shown in FIG. 26.

In FIG. 26, in the multilayer gas sensing element, generally designated at reference numeral 9, an oxygen pump cell 92 is located to confront a first measured gas chamber 11 and, upon receipt of a voltage, pumps oxygen existing in the interior of the first measured gas chamber 11 into the exterior of the sensing element, or pumps oxygen from the exterior of the sensing element into the interior of the first measured gas chamber 11.

In addition, an oxygen monitor cell 93 capable of detecting an oxygen concentration in the interior of the first measured gas chamber 11 is provided to feedback-control the oxygen pump cell 92 so that the oxygen concentration in the first measured gas chamber 11, detected by the oxygen monitor cell 93, becomes a steady state.

Still additionally, a sensor cell 94 is provided in a second measured gas chamber 12 communicating with the first measured gas chamber 11, with the sensor cell 94 being designed to measure a concentration of NOx by measuring an ionic current occurring due to oxygen ions generated through the decomposition of NOx on an electrode.

Since the oxygen concentration in the first measured gas chamber 11 is controlled to become a steady state as mentioned above, the oxygen concentration in the second measured gas chamber 12 becomes constant. Therefore, the quantity of oxygen ions moving between the electrodes in the sensor cell 94, that is, the magnitude of the oxygen ionic current in the sensor cell 94, corresponds to a concentration of NOx.

Thus, the NOx concentration of a measured gas introduced into the first and second measured gas chambers 11 and 12 can be measured with high accuracy irrespective of an increase/decrease in oxygen concentration in the atmosphere outside the sensing element.

Meanwhile, in the multilayer gas sensing element, not until the cells including the oxygen pump cell, the sensor cell and the monitor cell are heated up to an activating temperature, they can exhibits their functions.

For the heating thereof, as shown in FIG. 26, the multilayer gas sensing element 9 is equipped integrally with a heater 19 including a heat generator 191 for generating heat in response to current supply and a heater lead 192.

In this heater 19, in a case in which the difference in electrical resistance value between the heat generator 191 and the heater lead 192 is small, the heater lead 192 generates head up to a temperature close to that of the heat generator 109. For this reason, the temperature in the vicinity of the heater lead 192 rises and the electrical resistance value thereof decreases to create a situation in which a leakage current tends to flow.

In addition, in the multilayer gas sensing element, the current flowing through the oxygen monitor cell or the sensor cell is a minute current on the order of μA and, hence, the detection accuracy degrades even if a very small leakage current flows thereinto.

Furthermore, as a gas sensing element to be built in a gas sensor for combustion control of a vehicle engine and other applications, there have been known many elements such as an element disclosed in Japanese Patent No. 2885336.

A description will be given hereinbelow of one example of a gas sensing element for the engine combustion control or the like.

That is, as FIG. 27 shows, the gas sensing element, generally designated at reference numeral 509, is made up of a heater substrate 515, a heat generator 561 formed on the heater substrate 515 and made to generate heat when energized, a heater 506 including a heater lead (not shown) electrically connected to the heat generator 561, a spacer 514 for a reference gas chamber 5140 into which a reference gas is introduced, a pump cell solid electrolyte plate 513 for formation of a pump cell 502, a spacer 512 for a measured gas chamber 5122 into which a measured gas is introduced from the external, another slid electrolyte plate 511 for formation of a sensor cell 504 and a monitor cell 503, and a spacer 516 for another reference gas chamber 5160, with these components being built up (piled up) into a multilayer construction.

Also in this construction, the sensor cell 504 is for measuring a specified gas concentration such as NOx concentration of a measured gas and the monitor cell 503 is for monitoring an oxygen concentration of the measured gas. Moreover, as shown in FIGS. 28A and 28B, pump leads 5211 and 5221 of the pump cell 502 are provided at central portions in width directions of the pump cell solid electrolyte plate 513.

One of electrodes constituting the sensor cell 504 is placed in opposed relation to the measured gas chamber 5122 and a specified gas in the interior of the measured gas chamber 5122 is decomposed on an electrode surface so that the concentration of the specified gas is measured on the basis of a current produced by the generated oxygen ions. Likewise, the monitor cell 503 has an electrode confronting the measured gas chamber 5122 to ionize oxygen on a surface of the electrode for measuring an oxygen concentration utilizing a current of the generated oxygen ions.

However, a current flowing through the monitor cell 503 and the sensor cell 504 is very weak, usually below 10 μA. On the other hand, a current flowing through the heat generator 561 or the heater lead of the heater 506 is as extremely large as 10A or less.

In most gas sensing elements, an insulating material (in the construction shown in FIG. 27, the spacer 514 or 512 can be made of an insulating material) or the like is interposed between the heater 506 and the electrodes of the sensor cell 504 or the monitor cell 503 to increase the electrical resistance of an electrical path formed between the heater 506 and the sensor cell 504 or the monitor cell 503. However, difficulty is experienced in reducing the leakage current to zero between the heater 506 and the sensor cell 504 or the monitor cell 503.

In addition, since the oxygen ionic current flowing through the sensor cell 504 or the monitor cell 503 is very weak as mentioned above, the effect of a small leakage current is not ignorable, and the leakage current causes the deterioration of measurement accuracy of the gas sensing element.

SUMMARY OF THE INVENTION

The present invention has been developed in consideration of these conventional problems, and it is therefore an object of the invention to provide a multilayer gas sensing element having a high detection accuracy and less susceptible to the influence of a leakage current, and to provide a gas sensing element whose measurement accuracy is less susceptible to the leakage current from the heater.

For this purpose, in accordance with an aspect of the present invention, there is provided a multilayer gas sensing element comprising a measured gas chamber into which a measured gas is introduced under a predetermined diffusion resistance, an oxygen pump cell having a pair of electrodes placed on surfaces of an oxygen ionic conductive solid electrolyte plate so that one of the pair of electrodes confronts the measured gas chamber, and made to, when the pair of electrodes are energized, introduce or discharge oxygen into or from the measured gas chamber for adjusting an oxygen concentration in the interior of the measured gas chamber, a sensor cell having a pair of electrodes placed on surfaces of an oxygen ionic conductive solid electrolyte plate so that one of the pair of electrodes confronts the measured gas chamber and made to detect a specified gas concentration in the interior of the measured gas chamber on the basis of an oxygen ionic current occurring between the pair of electrodes, and a heater for heating the oxygen pump cell and the sensor cell up to an activating temperature, wherein the heater includes a heat generator for generating heat when energized, a heater terminal located in the exterior of the multilayer gas sensing element and a heater lead for making an electrical connection between the heat generator and the heater terminal, and when an electrical resistance value of the heat generator is taken as RH and an electrical resistance value of the heater lead is taken as RL, the values RH and RL are set to satisfy the relationship of $1.5 \leq RH/RL$.

A description will be given hereinbelow of the effects of the present invention.

In the multilayer gas sensing element according to the present invention, the relationship of $1.5 \leq RH/RL$ is satisfied between the electrical resistance value RH of the heat generator and the electrical resistance value RL of the heater lead. Upon receipt of the supply of a current, each of the heat generator and the heater lead generates heat according to its electrical resistance value. Assuming that the electrical resistance value of the heat generator is relatively low with respect to that of the heater lead, the quantity of heat generated from the heater lead becomes relatively large.

Moreover, in general, in the case of a ceramic material such as alumina or zirconia, its electrical resistance value drops with a rise of temperature so that the current becomes easy to flow. For this reason, a portion at which the electrical resistance value drops due to the heating by the heater lead tends to form a leakage current path.

According to the present invention, the electrical resistance value of the heater lead is set to fall below RH/1.5 with respect to that of the heat generator to reduce the heat quantity to be generated in the heater lead for lowering the temperature in the vicinity of the heater lead, thereby reducing the portion which tends to become a leakage current path to suppress the occurrence of a leakage current for reducing the influence of the leakage current on the sensor cell.

Accordingly, the present invention can provide a multilayer gas sensing element having a high detection accuracy and less susceptible to the influence of the leakage current.

In a multilayer gas sensing element according to the present invention, a heat generator and a heater lead are made in the form of a patterned thin conductive layer on a substrate (for example, see FIG. 3).

In the multilayer gas sensing element, the heat generator principally produces a large heat quantity when energized, thereby heating an oxygen pump cell, a sensor cell, an oxygen monitor cell, other solid electrolyte plates whose operating states are influenced by temperature, and various electrochemical cells (for example, a second pump cell in a fourth embodiment) each comprising a pair of electrodes up to an activating temperature at which they can operate, or maintaining the activating temperature.

Moreover, as illustrated in FIGS. 3 to 6, the heat generator is made to more easily generate heat as compared with the heater lead. The heater lead is made to have a large width attaching great importance to an easy flow of current.

In the multilayer gas sensing element according to the present invention, preferably, the upper limit of RH/RL is set to be 10. If it exceeds this value, the overall electrical resistance value including those of the heat generator and the heater lead becomes too high and there is a possibility that the voltage to be applied becomes excessively high. Preferably, $2 \leq RH/RL \leq 5$.

The multilayer gas sensing element according to the present invention is applicable to a NOx sensor element, CO sensor element or HC sensor element which has two or more cells.

Preferably, the heat generator and the heater lead are made of materials different in electrical resistance value from each other. This enables easy adjustment of the electrical resistance values of the heat generator and the heater lead.

In a case in which the electrical resistance value is changed by changing the material to be used, it is preferable that the heat generator and the heater lead are made of a cermet material comprising a metallic particle containing Pt and a ceramic particle containing alumina and the content of the ceramic particle in the cermet material producing the heat generator is larger than the content of the ceramic particle in the cermet material producing the heater lead.

The metallic particle is an electric conductor while the ceramic particle is an insulating material, and when both are mixed to properly adjust the contents thereof, the heat generator and the heater lead can easily be produced to have predetermined electrical resistance values.

In addition, the body of the heater is generally made of alumina, and when the heat generator or the lead contains the same material, the junction therebetween is improvable to reduce the troubles such as peeling.

Preferably, the content of the ceramic particle of the cermet material for the heat generator is set at 5 to 15 wt %. If the content of the ceramic particle falls below 5 wt %, the junction characteristic with the body of the heater can degrade moreover, since the heat generator is frequently formed to have a narrow width, if the content of the ceramic particle exceeds 15 wt %, disconnection can occurs.

Still additionally, as the metallic particle containing Pt, a powder of only Pt particle or a powder of a mixture of Pt and Rh (rhodium) is available.

Yet additionally, as the ceramic particle containing alumina, a ceramic particle made of an alumina powder or a powder of a mixture of alumina and zirconia is available.

Preferably, the thickness of the heat generator is thinner (Gower) than the thickness of the heater lead.

This can easily produce a heat generator and a heater lead each of which has a desired electrical resistance value. Moreover, the heat generator and the heater lead are made of the same cermet material, which facilitates the manufacturing thereof.

Preferably, the thickness of the heat generator is 20 to 70 μm. If the thickness thereof falls below 20 μm, there is a possibility that disconnection occurs or the electrical resistance value increases excessively to cause the voltage to be applied to become excessively high. On the other hand, if the thickness thereof exceeds 70 μm, difficulty can be experienced in forming its pattern uniformly.

Furthermore, preferably, the gas sensing element further comprises an oxygen monitor cell including a pair of electrodes provided on a surface of an oxygen ionic conductive solid electrolyte plate so that one of the pair of electrodes confronts the measured gas chamber, and made to detect an oxygen concentration in the interior of the measured gas chamber on the basis of a current or electromotive force occurring between the pair of electrodes. This enables monitoring the oxygen concentration in the measured gas chamber.

Still furthermore, in addition to, for example, an arrangement whereby an operation of the oxygen pump cell is controlled so that the oxygen concentration in the measured gas chamber falls within a predetermined range, the multilayer gas sensing element has an arrangement whereby an oxygen ionic current flowing between a pair of electrodes of a sensor cell corresponds more accurately to a specified gas concentration to be measured.

In this connection, the oxygen monitor cell made to detect an oxygen concentration on the basis of a current value is designed to function as a limiting current type oxygen sensor, while the oxygen monitor cell made to detect an oxygen concentration on the basis of an electromotive force is designed to function as an oxygen concentration electromotive force type oxygen sensor (see FIG. 1).

In addition, in accordance with a further aspect of the present invention, there is provided a gas sensing element comprising a heater including a heater substrate, a heat generator provided on the heater substrate for generating heat when energized and a heater terminal electrically connected through a heater lead to the heat generator, a spacer for a measured gas chamber into which a measured gas is introduced from the external, a spacer for a reference gas chamber into which a reference gas is introduced, a solid electrolyte plate including an electrochemical cell having a pair of electrodes for detecting a specified gas concentration on the basis of a minute current stemming from oxygen ions and flowing between the pair of electrodes, which are built up into a multilayer construction, wherein a leakage current conducting path is provided in the middle of an electrical path between the heater and the electrochemical cell for leading a leakage current from the heater to a portion other than the electrochemical cell.

In the gas sensing element according to the present invention, a leakage current conducting path is formed in a place which can be used as a path for a leakage current between the heater and the electrochemical cell, that is, in the middle of an electrical path therebetween. Therefore, the leakage current is let out through the leakage current conducting path without reaching the electrochemical cell.

In this connection, the electrical path is formed in a sold portion including the solid electrolyte plate residing between the heater and the electrochemical cell. Even if an insulating material exists between the heater and the electrochemical cell as will be described later in a fifth embodiment of the present invention, a minute leakage current can flow in this insulating material portion and, hence, this insulating material portion can also serve as an electrical path.

Thus, this can provide a gas sensing element which is less susceptible in measurement accuracy to the leakage current from the heater.

In the present invention, the electrochemical cell is a cell in which the magnitude of an oxygen ionic current flowing between the electrodes falls below 10 μA. In the case of a gas sensing element for the measurement of NOx, oxygen concentration and λ point according to the fifth embodiment which will be described later, a sensor cell for measuring a NOx concentration of a measured gas, a monitor cell for monitoring an oxygen concentration of the measured gas and a λ cell for detecting a λ point through the use of a measured gas in the exterior of the gas sensing element correspond to the "electrochemical cell for detecting a specified gas concentration in the measured gas chamber on the basis of a minute current stemming from oxygen ions and flowing between the pair of electrodes".

Moreover, the present invention is also applicable to, in addition to the NOx concentration measurement, a gas sensing element made to measure an HC concentration or a CO concentration. In this case, the sensor cell for the measurement of the HC concentration or the CO concentration corresponds to the "electrochemical cell for detecting a specified gas concentration in the measured gas chamber on the basis of a minute current stemming from oxygen ions and flowing between the pair of electrodes".

Still moreover, the oxygen sensor cell for the measurement of an oxygen concentration of a measured gas in the gas sensing element, which is made to measure oxygen concentration, also comes under the electrochemical cell according to the present invention.

This oxygen sensor cell is equipped with electrodes confronting a measured gas chamber and a reference gas chamber, respectively, and is classified into a cell designed to measure an oxygen concentration on the basis of an electromotive force occurring between both electrodes and a cell designed to measure an oxygen concentration on the basis of a limiting current occurring when a voltage is applied to both electrodes.

Furthermore, when the aforesaid leakage current conducting path is formed to overlap partially with an electrical path, such as crossing a portion constituting the electrical path, the effects of the present invention are attainable.

Still furthermore, when the leakage current conducting path is electrically grounded, the leakage current can more surely be led to the leakage current conducting path side. Yet moreover, preferably, the leakage current conducting path is made of a material having a lower electrical resistance than that of the electrical path through which the leakage current flows, and is made with a high-quality electrical conductor.

In addition, preferably, the aforesaid gas sensing element comprises a pump cell composed of a pump cell solid electrolyte plate and a pair of pump electrodes provided on the pump cell solid electrolyte plate for pumping oxygen with respect to the measured gas chamber, and the pump cell solid electrolyte plate includes pump leads electrically connected (conducted) to the pair of pump electrodes and the pump leads are electrically connected to terminals exposed to the exterior of the gas sensing element, with the leakage current conducting path being made with the pump leads.

A current flowing through the pump cell is below 10 mA (on the order of mA), and the flowing of a leakage current thereinto is ignorable. Moreover, the function of the pump cell is to introduce or eject oxygen into and from the measured gas chamber for adjusting the oxygen concentration in the measured gas chamber to a predetermined value. Still moreover, the function thereof is to eject oxygen from the measured gas chamber so that the oxygen approaches zero to the utmost. Accordingly, the measurement accuracy of the gas sensing element hardly depends upon the magnitude of the current flowing through the pump cell.

For this reason, even if the pump leads also serve as the leakage current conducting path, the operation of the pump cell is not affected and a minimum specification alteration from the conventional construction is acceptable, which can reduce the number of parts accordingly as compared with a case of the employment of separate parts. This is advantageous in manufacturing cost or the like.

In this connection, the pump leads are used as a conducting path for making connections between the pump electrodes of the pump cell and the terminals provided in a state exposed to the exterior of the gas sensing element for the connections to a power source for driving the pump cell and others.

Moreover, preferably, the heater, the reference gas chamber spacer, the pump cell solid electrolyte plate and the measured gas chamber spacer are built up in a state adjacent to each other, and one pump lead is located in a first boundary surface between one outer surface of the gas sensing element and an inner surface of the reference gas chamber and between the pump cell solid electrolyte plate and the reference gas chamber spacer, while the other pump lead is located in a second boundary surface between the other outer surface of the gas sensing element and an inner surface of the measured gas chamber and between the pump cell solid electrolyte plate and the measured gas chamber spacer.

In a case in which the spacers and the pump cell electrolyte plate are built up in the above-mentioned order, a leakage current form the heater passes through the reference gas chamber spacer, the pump cell solid electrolyte plate and the measured gas chamber spacer in the built-up direction and then reaches the electrochemical cell solid electrolyte plate.

Therefore, the first and second boundary surfaces are positioned to cross the electrical path between the heater and the electrochemical cell. When the pump leads are located at the first and second boundary surfaces, the leakage current flows to the pump leads, thereby preventing the leakage current from arriving at the electrochemical cell.

Still moreover, when a minimum width of the first boundary surface along a cross direction perpendicular to a longitudinal direction of the gas sensing element is taken to be A, a maximum width of the pump lead located at the first boundary surface along the cross direction is taken as a, a minimum width of the second boundary surface along the cross direction is taken as C and a maximum width of the pump lead located at the second boundary surface along the cross direction is taken as c, it is preferable that $0.1 \leq a/A$, $0.1 \leq c/C$.

Thus, the pump leads capable of leading the leakage current more effectively is obtainable.

In the case of a/A and c/C being below 0.1, difficulty can be encountered in leading the leakage current because they becomes too thin.

Preferably, the upper limits of a/A and c/C are set at 0.99. If the upper limits exceed this value, the measured gas is put in the measured gas chamber serving as a current path from the exterior of the gas sensing element and, hence, there is a possible that the pumping action becomes insufficient, for example, difficulty is encountered in sufficiently ejecting oxygen forming an interfering gas (which hinders the measurement of a specified gas concentration in the sensor cell) through the use of the pump cell. Moreover, there is a possibility that the concentration of a specified gas to be concentration-measured in the sensor cell varies. Still moreover, peeling can occur at the first boundary surface or the second boundary surface.

In addition, it is preferable that the pump leads are buried in order to prevent them from coming into contact with a measured gas at an outer surface of the gas sensing element.

Still additionally, the aforesaid gas sensing element comprises a pump cell including a pump cell solid electrolyte plate and a pair of pump electrodes provided on the pump cell solid electrolyte plate for pumping oxygen with respect to the measured gas chamber, and the pump electrodes are made to cover an electrode projection plane formed by projecting a pair of electrodes for the electrochemical cell onto the pump cell solid electrolyte plate, and the aforesaid leakage current conducting path is made through the use of the pump electrodes.

When the pump electrodes are extendedly formed in this way, it is possible to provide a positional relationship of the pump electrodes crossing the leakage current electrical path.

Usually, a current flowing through the pump cell is below 10 mA (on the order of mA), and the flowing of a leakage current thereinto is ignorable. Moreover, the function of the pump cell is to introduce or eject oxygen into and from the measured gas chamber for adjusting the oxygen concentration in the measured gas chamber to a predetermined value. Still moreover, the function thereof is to eject oxygen from the measured gas chamber so that the oxygen approaches zero to the utmost. Accordingly, the measurement accuracy of the gas sensing element hardly depends upon the magnitude of the current flowing through the pump cell.

For this reason, even if the pump electrodes also serve as the leakage current conducting path, the operation of the pump cell is not affected and a minimum specification alteration from the conventional construction is acceptable, which reduce the number of parts accordingly as compared with a case of the employment of separate parts. This is advantageous in manufacturing cost or the like.

In this connection, if at least one of the pair of pump electrodes is constructed as mentioned above, the effects of the present invention are achievable.

Furthermore, it is preferable that the leakage current conducting path is made using a conductive layer placed on the heater in a state where an insulating plate is interposed therebetween.

Thus, the conductive layer crosses the electrical path between the heater and the electrochemical cell so that the leakage current flows through the conductive layer without reaching the electrochemical cell. Accordingly, the effects of the present invention are more surely attainable.

Still furthermore, when the width of the gas sensing element along a cross direction perpendicular to the longitudinal direction of the gas sensing element is taken as B and the width of the aforesaid conductive layer is taken as b, it is preferable that $0.5 \leq b/B$.

This more effectively makes the leakage current flow through the conductive layer.

If b/B falls below 0.1, the width of the conductive layer becomes too small, which can cause the leakage current to be hard to flow.

Moreover, the upper limit of b/B is 0.99. If it exceeds this value, the peeling of the gas sensing element can occur at the conductive layer portion. In this case, values b and B are average values.

Still moreover, preferably, the leakage current conducting path is made of a material containing at least a noble metal or of a cermet containing a noble metal and ceramics.

This can provide a leakage current conducting path forming a high-quality electrical conductor permitting easy flowing of the leakage current.

As the aforesaid noble metal, Pt, Au, Rh and Pd are available. As the ceramics, alumina, zirconia and others are usable.

BRIEF DESCRIPTION OF THE DRAWINGS

Other objects and features of the present invention will become more readily apparent from the following detailed description of the preferred embodiments taken in conjunction with the accompanying drawings in which:

FIG. 16 is a graphic illustration of temperature dependency of offset current in the fifth embodiment and a conventional example;

DESCRIPTION OF THE PREFERRED EMBODIMENTS

Embodiments of the present invention will be described hereinbelow with reference to the drawings.

First Embodiment

Figure 1A:
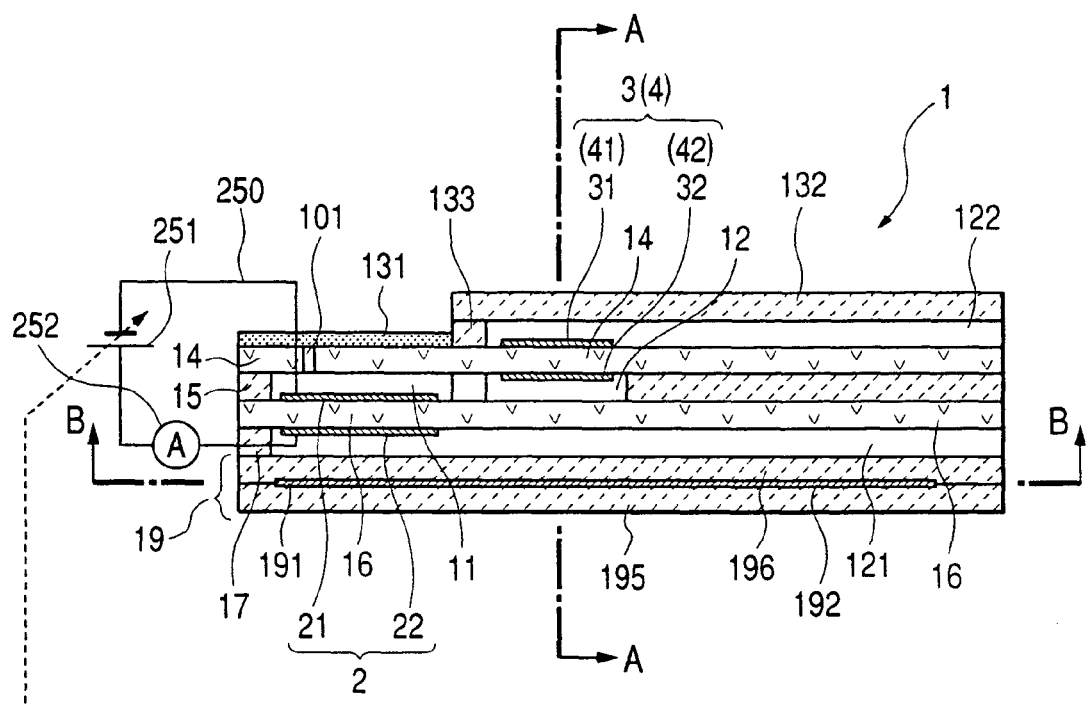
FIG. 1A is a longitudinal cross-sectional view showing a multilayer gas sensing element according to a first embodiment of the present invention.
Figure 1B:
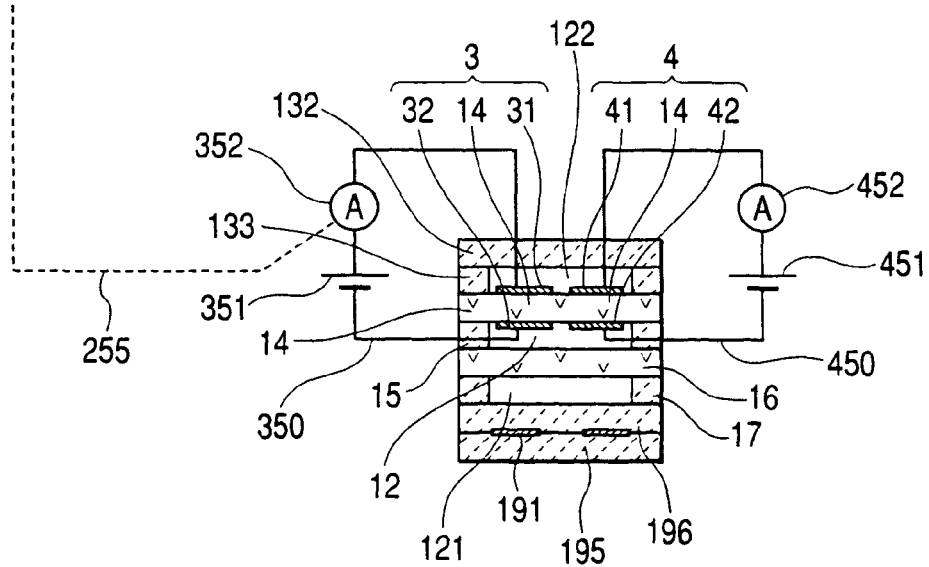
FIG. 1B is a transverse cross-sectional view taken along an arrow-indicated line A-A of FIG. 1A.
Figure 2:
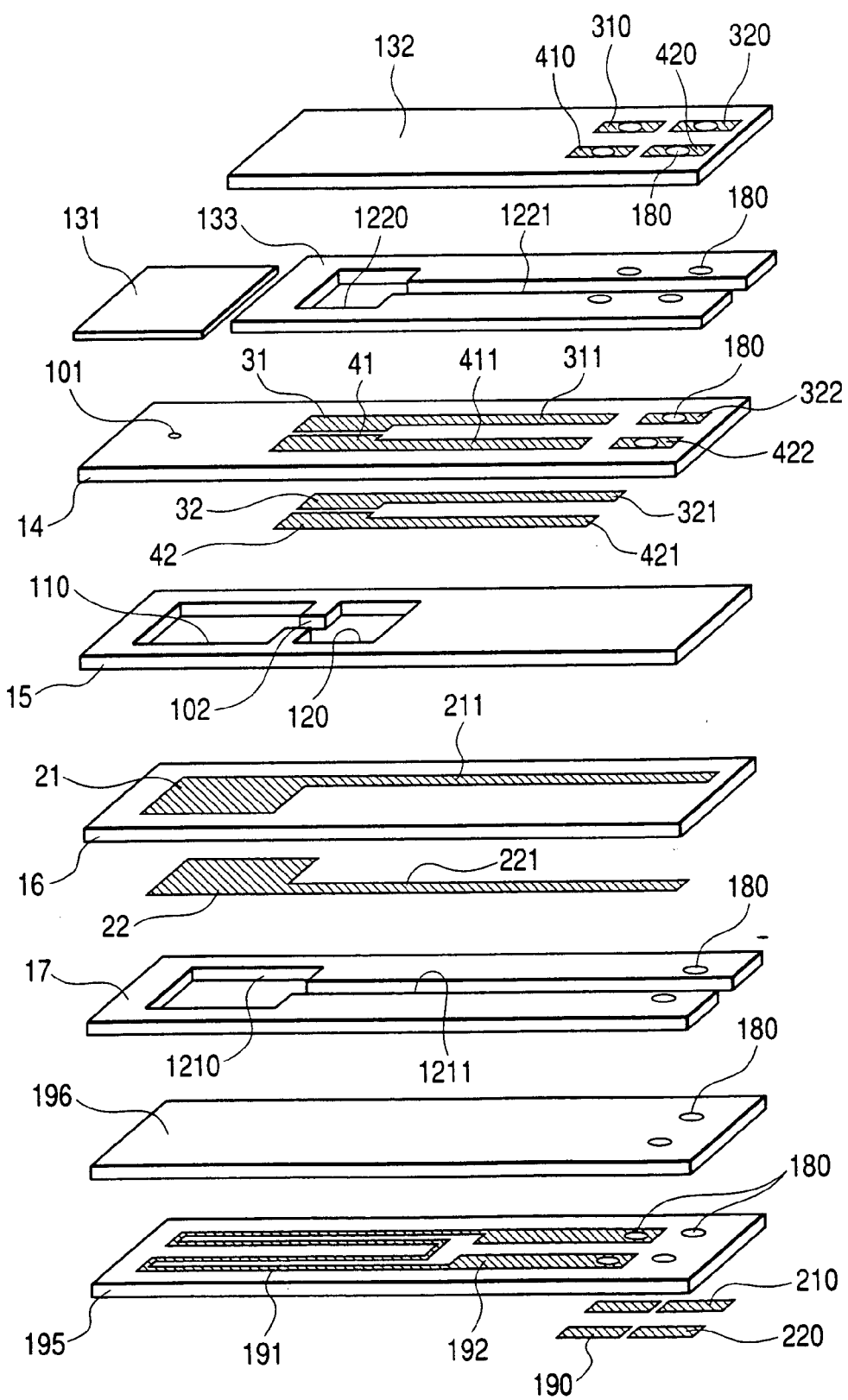
FIG. 2 is a perspective development elevation showing the multilayer gas sensing element according to the first embodiment.

A description will be given hereinbelow of a multilayer gas sensing element according to a first embodiment of the present invention. As shown in FIGS. 1A, 1B and 2, a multilayer gas sensing element according to this embodiment, generally designated at reference numeral 1, is made up of first and second measured gas chambers 11 and 12 into which a measured gas is introduced under a predetermined diffusion resistance, an oxygen pump cell 2 including a pair of electrodes 21 and 22 provided on surfaces of an oxygen ionic conductive solid electrolyte plate 16 so that one electrode 21 confronts the first measured gas chamber 11 and made to, when the pair of electrodes 21 and 22 are energized, introduce or discharge oxygen into or from the first measured gas chamber 11 for adjusting an oxygen concentration in the interior of the first measured gas chamber 11, a sensor cell 4 including a pair of electrodes 41 and 42 provided on surfaces of an oxygen ionic conductive solid electrolyte plate 14 so that one electrode 42 confronts the second measured gas chamber 12 and made to detect a specified gas concentration (NOx in this embodiment) in the interior of the second measured gas chamber 12 on the basis of an oxygen ionic current occurring between the pair of electrodes 41 and 42, and a heater 19 for heating the oxygen pump cell 2 and the sensor cell 4 up to an activating temperature.

The heater 19 includes a heat generator (heating element) 191 for generating heat when energized, a heater terminal 190 provided in the exterior of the multilayer gas sensing element 1, and a heater lead 192 for making electrical connection between the heat generator 191 and the heater terminal 190.

When the electrical resistance value of the heat generator 191 is taken to be RH and the electrical resistance value of the heater lead 192 is taken as RL, the relationship of $1.5 \leq RH/RL$ is satisfied.

A detailed description will be given hereinbelow of the multilayer gas sensing element 1 according to this embodiment.

The multilayer gas sensing element 1 is constructed such that, as shown in FIGS. 1A, 1B and 2, built up sequentially are the sheet-like solid electrolyte plate 16, the sheet-like solid electrolyte plate 14 for forming an oxygen monitor cell 3, the sensor cell 4, a sheet-like spacer 15 for forming the first measured gas chamber 11 and the second measured gas chamber 12, sheet-like spacers 17, 133 and 132 for forming reference gas chambers 121 and 122 and the heater 19 for heating the cells 2, 3 and 4.

Each of the first and second measured gas chambers 11 and 12 is an internal chamber into which a gas to be measured is introduced from the exterior of the element 1 and, as shown in FIG. 2, are formed using two punched holes 110 and 120 made in the spacer 15 residing between the solid electrolyte plates 14 and 16. Between the punched holes 110 and 120, there is formed an area reduction portion 102 having a width narrower than those of the through holes 110 and 120. Due to this area reduction portion 102, the first measured gas chamber 11 and the second measured gas chamber 12 are formed by the punched holes 110 and 120, respectively, with the first measured gas chamber 11 being positioned on the tip side (on the left side in FIGS. 1A and 2) of the multilayer gas sensing element 1.

In addition, the first measured gas chamber 11 communicated through a pinhole 101 passing through the solid electrolyte plate 14 and serving as a diffusion resistance means with the exterior of the element 1.

The diameter of the pinhole 101 is properly set so that the diffusion speed of the measured gas which is introduced through the pinhole 101 into the first measured gas chamber 11 and the second measured gas chamber 12 becomes a predetermined value.

Still additionally, on the solid electrolyte plate 14, a porous protective layer 131 made of porous alumina or the like is formed to cover an opening of the pinhole 101. This prevents the poisoning of the electrodes 21, 32 and 42 existing in the interior of the first and second measured gas chambers 11 and 12 and the clogging of the pin hole 101.

Each of the reference gas chambers 121 and 122 is an internal chamber into which the atmospheric air is introduced as a reference oxygen concentration gas having a constant oxygen concentration.

The reference gas chamber 121 is defined by a punched hole 1210 made in the spacer 17 located below the solid electrolyte plate 16, while the reference gas chamber 122 is defined by a punched hole 1220 made in the spacer 133 located above the solid electrolyte plate 14.

These punched holes 1210 and 1220 respectively have passage portions 1211 and 1221 which extend in longitudinal directions of the multilayer gas sensing element 1, and the atmospheric air can be introduced through the passage portions 1211 and 1221.

The oxygen pump cell 2 is composed of the solid electrolyte plate 16 and the pair of electrodes 21 and 22 located in opposed relation to each other in a state where the solid electrolyte plate 16 is interposed therebetween.

Of the pair of electrodes 21 and 22, the electrode 21 is placed into contact with the solid electrolyte plate 16 to confront, of the first and second measured gas chambers 11 and 12, the first measured gas chamber 11 existing on the upstream side in the gas flowing direction, while the other electrode 22 is brought into contact with the solid electrolyte plate 16 to confront the reference gas chamber 121.

The sensor cell 4 is composed of the solid electrolyte plate 14 and the pair of electrodes 41 and 42 located in opposed relation to each other in a state where the solid electrolyte plate 14 is interposed therebetween.

Of the pair of electrodes 41 and 42, one electrode 42 is placed into contact with the solid electrolyte plate 14 to face, of the first and second measured gas chambers 11 and 12, the second measured gas chamber 12 positioned on the downstream side in the gas flowing direction, while the other electrode 41 is placed on the solid electrolyte plate 14 to face the reference gas chamber 122.

The oxygen monitor cell 3 is made up of the solid electrolyte plate 14 and the pair of electrodes 31 and 32 placed in opposed relation to each other with the solid electrolyte plate 14 being interposed therebetween.

Of the pair of electrodes 31 and 32, one electrode 32 is placed on the solid electrolyte plate 14 to confront, of the first and second measured gas chambers 11 and 12, the second measured gas chamber 12 existing on the downstream side in the gas flowing direction, while the other electrode 31 is placed on the solid electrolyte plate 14 to be in opposed relation to the reference gas chamber 122.

In addition, as shown in FIG. 2, electrode lead portions 211, 221, 311, 321, 411 and 421 are formed integrally with the above-mentioned electrodes 21, 22, 31, 32, 41 and 42, respectively, for deriving electric signals or for supplying electric power from a power source.

Still additionally, preferably, in areas other than the electrode 21 and others on the solid electrolyte plates 14 and 16, particularly in the formation areas of the electrode lead portion 211 and others, insulating layers (not shown), such as alumina, are formed between the solid electrolyte plates 14, 16 and the electrode lead portions 211, 321, 421 and others.

Yet additionally, as shown in FIG. 2, the electrodes 21, 22, 31, 32, 41 and 42 of the cells 2, 3 and 4 are electrically connected through the lead portions 211, 221, 311, 321, 411 and 421 and through holes 180 made in the spacers 17 and others to external terminal portions 310, 320, 410, 420, 210 and 220 formed in the exterior of the multilayer gas sensing element 1 in a state exposed.

When the external terminal portions 310, 320, 410, 420, 210 and 220 are connected through suitable connectors to lead wires by means of attachment under pressure, brazing or the like, electric signals can be interchanged between external circuits (which will be mentioned in detail later) and the cells 2, 3 and 4.

Reference numerals 322 and 422 denote internal terminals connected to the electrode lead portions 321 and 421, respectively.

The oxygen pump cell 2, the oxygen monitor cell 3 and the sensor cell 4 are connected through the above-mentioned external terminal portions (310 and others) to a pump circuit 250 equipped with a pump power source 251 and an ammeter 252, a monitor circuit 350 equipped with a power source 351 and an ammeter 352 and a sensor circuit 450 equipped with a power source 451 and an ammeter 452, respectively.

The heater 19 is provided in order to make the heat generator 191 generate heat in response to the power from the external power source (not shown) for heating each of the cells 2, 3 and 4 up to an activating temperature.

For the production of the heater 19, the heat generator 191 made to generate heat when energized is patterning formed on an upper surface of an alumina-made heater substrate 195 and a coating plate 196 for the insulation is placed on an upper surface (spacer 17 side surface) of the heat generator 191.

Figure 3:
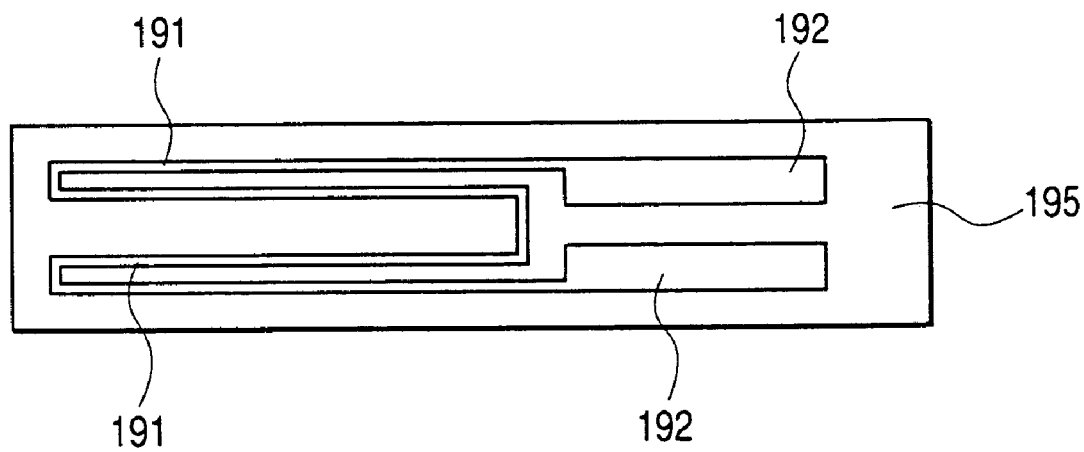
FIG. 3 is a cross-sectional plan view taken along an arrow-indicated line B-B, showing first configurations of a heat generator and a heater lead in a heater according to the first embodiment.

FIG. 3 is an illustration of configurations of the heat generator 191 and the heater lead 192 in the heater 19. The heat generator 191 is formed to have a small (narrow) width while the heater lead 192 is formed to have a large (wide) width, and as obvious from FIG. 2, the formation position of the heat generator 191 is just under the formation positions of the cells 2, 3 and 4.

Moreover, although not shown, heater terminal portions 190 of the heater 19 are connected to a heater circuit including a heater power source.

In this connection, as shown in FIG. 2, the heater terminal portions 190 and the external terminal portions 210 and 220 are provided on the heater 19 side surface (Gower surface in the illustration) of the multilayer gas sensing element 1 while the external terminal portions 310, 320, 410 and 420 are provided on the spacer 132 side surface (upper surface in the illustration) thereof.

Secondly, a description will be given hereinbelow of the compositions of the respective parts of the multilayer gas sensing element thus constructed.

Each of the spacers 17, 15, 133 and 132 is made of an insulating material such as alumina, and each of the solid electrolyte plates 14 and 16 forming the oxygen pump cell 2, the oxygen monitor cell 3 and the sensor cell 4 is made of ceramics, such as zirconia or ceria, having an oxygen ionic conductive property.

Preferably, as one electrodes 21 and 32 of the oxygen pump cell 2 and the oxygen monitor cell 3, an electrode having a low NOx decomposition activity is employed in order to suppress the decomposition of NOx in the first and second measured gas chambers 11 and 12. Concretely, a porous cermet electrode containing Pt and Au is preferable. In this case, in the porous cermet electrode, it is preferable that the content of Au of the metallic component is approximately 1 to 10 wt %.

Moreover, preferably, as the electrode 42 of the sensor cell 4 confronting the second measured gas chamber 12, an electrode having a high NOx decomposition activity is employed in order to decompose NOx of the measured gas. Concretely, a porous cermet electrode containing Pt and Rh is preferable. In this case, in the porous cermet electrode, it is preferable that the content of Rh of the metallic component is approximately 10 to 50 wt %.

The solid electrolyte plates 14, 16, the spacers 15, 17, 133, 132, the alumina insulating plate 196 and the heater sheet 195 can be formed into a sheet configuration by means of the doctor blade method, extrusion molding method or the like.

Still moreover, each of the above-mentioned electrodes, such as the electrode 21, the aforesaid lead portions such as the lead portion 211 and the aforesaid terminal portions such as the terminal portion 210 can be formed through the use of the screen printing or the like. The respective sheets can be integrated with each other when being built up and calcined.

Yet moreover, preferably, for example, a Pt porous cermet electrode is employed as the electrodes 22, 31 and 41 of the oxygen pump cell 2, the oxygen monitor cell 3 and the sensor cell 4 which confront the reference gas chambers 121 and 122.

In addition, each of the heat generator 191 and the heater lead 192 is made of a cermet material comprising Pt and ceramics containing alumina.

The composition of the cermet material for the heat generator 191 is such that Pt:85 wt % and alumina-contained ceramics:15 wt %. The composition of the cermet material for the heater lead 192 is such that Pt:90 wt % and alumina-contained ceramics:10 wt %.

Still additionally, the electrical resistance value RH of the heat generator 191 is set to be 1.5 Ω while the electrical resistance value RL of the heater lead 192 is set at 0.5 Ω.

Furthermore, a description will be given hereinbelow of the principle of operation of the gas sensing element thus constructed.

A gas to be measured is introduced into the first measured gas chamber 11 after passing through the porous protective layer 131 and the pinhole 101. At this time, the quantity of the gas to be introduced thereinto depends upon the diffusion resistances of the porous protective layer 131 and the pinhole 101. Following this, the measured gas passes through the area reduction portion 102 and comes in the second measured gas chamber 12.

In a case in which a voltage is applied from the pump power source to the pair of electrodes 21 and 22 of the oxygen pump cell 2 so that the electrode 22 residing on the reference gas chamber 121 side becomes plus pole, the oxygen of the measured gas is reduced on the electrode 21 residing on the first measured gas chamber 11 side to become oxygen ions which in turn, are discharged to the electrode 22 side by means of the pumping action.

Conversely, when the voltage application takes place so that the electrode 21 on the first measured gas chamber 11 side becomes plus pole, the oxygen is reduced on the electrode 22 on the reference gas chamber 121 side and the produced oxygen ions are ejected through the pumping action toward the electrode 21 side.

Thus, the oxygen concentrations in the first measured gas chamber 11 and the second measured gas chamber 12 communicating therewith can be controlled through the use of the oxygen pumping function.

When a predetermined voltage (for example, 0.40V) is applied to the pair of electrodes 31 and 32 of the oxygen monitor cell 3 so that the electrode 31 on the reference gas chamber 122 side becomes plus pole, the oxygen of the measured gas is reduced on the electrode 32 on the second measured gas chamber 12 side to produce oxygen ions which in turn, are ejected to the electrode 31 side by means of the pumping function.

Since the electrode 32 is a Pt—Au cermet electrode inactive for the decomposition of NOx, the oxygen ionic current flowing between the electrodes 31 and 32 passes through the porous protective layer 131, the pinhole 101, the first measured gas chamber 11 and others, and depends upon the quantity of oxygen of the measured gas arriving at the electrode 32 but not depending on the quantity of NOx.

Accordingly, if the voltage to be applied between the electrodes 21 and 22 of the oxygen pump cell 2 is controlled so that the current value between the electrodes 31 and 32 becomes constant vale (for example, 0.2 µA), the second measured gas chamber 12 is controllable to become a constant or given oxygen concentration at all times.

A predetermined voltage (for example, 0.40V) is applied to the pair of electrodes 41 and 42 of the sensor cell 4 so that the electrode 41 on the reference gas chamber 122 side becomes plus pole. Since the electrode 42 is a Pt—Rh cermet electrode active with respect to the decomposition of NOx, the oxygen and NOx of the measured gas are reduced on the electrode 42 on the second measured gas chamber 12 side to produce oxygen ions, with the produced oxygen ions being ejected toward the electrode 41 side by means of the pumping action.

In addition, as shown in FIGS. 1A and 1B, in the multilayer gas sensing element 1 according to this embodiment, the oxygen pump cell 2 is controlled so that the current value between the electrodes 31 and 32 of the oxygen monitor cell 3 becomes a constant value (for example, 0.2 µA).

At this time, if NOx is absent in the measured gas, the current value between the electrodes 41 and 42 of the sensor cell 4 also becomes a constant value (for example, 0.2 µA). On the other hand, if NOx is present in the measured gas, the current value increases with the NOx concentration. This enables the detection of the NOx concentration of the measured gas.

Furthermore, a description will be given hereinbelow of the effects of this embodiment.

In a case in which the electrical resistance value of the heat generator 191 is relatively low with respect to that of the heater lead 192, the quantity of heat from the heater lead 192 becomes large.

As obvious from FIG. 2, in the multilayer gas sensing element 1 according to this embodiment, above the heater lead 192, there exist the lead portions 421, 321 and others electrically connected to the pairs of electrodes 41, 42 and 31, 32 of the sensor cell 4 and the oxygen monitor cell 3. For this reason, leakage currents tend to develop between the electrode lead portions or between the external terminal portions due to the heat generation of the heater lead 192.

In particular, in the case of the configuration according to this embodiment, since the through hole 180 is made to pass through the solid electrolyte plate 14, the spacer 17 and others, if the temperature of a portion of the solid electrolyte plate 14 or the spacer 17 just above the heater lead 192 rises, the leakage current appears easily.

In the multilayer gas sensing element 1 according to this embodiment, the electrical resistance value RH of the heat generator 191 is set at 1.5 Ω and the electrical resistance value RL of the heater lead 192 is set at 0.5 Ω, thereby satisfying the relationship of 1.5≦RH/RL. Therefore, the leakage current becomes difficult to generate just above the heater lead 192, which leads to more accurate concentration measurement (see second embodiment).

As described above, according to this embodiment, a multilayer gas sensing element is attainable which is less susceptible to the influence of the leakage current and has a high detection accuracy.

Figure 4:
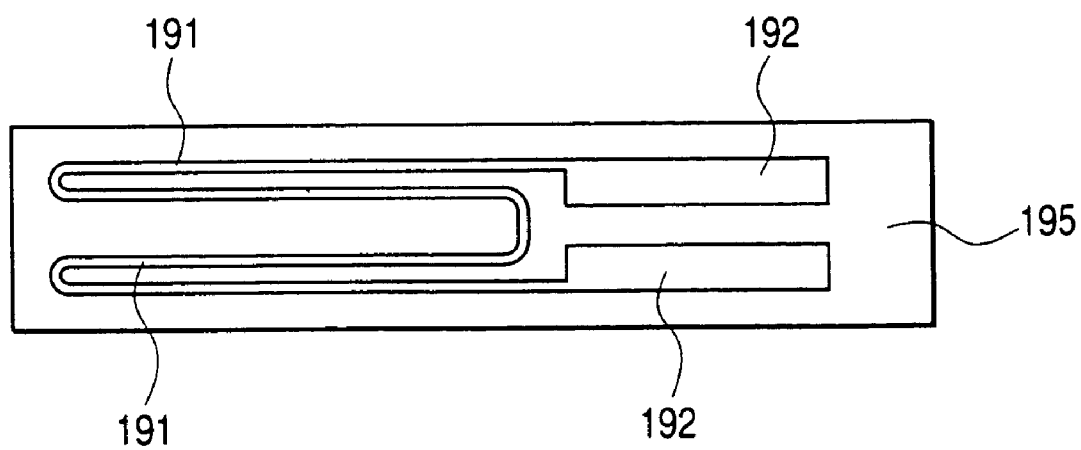
FIG. 4 is a plan view showing second configurations of the heat generator and the heater lead according to the first embodiment.
Figure 5:
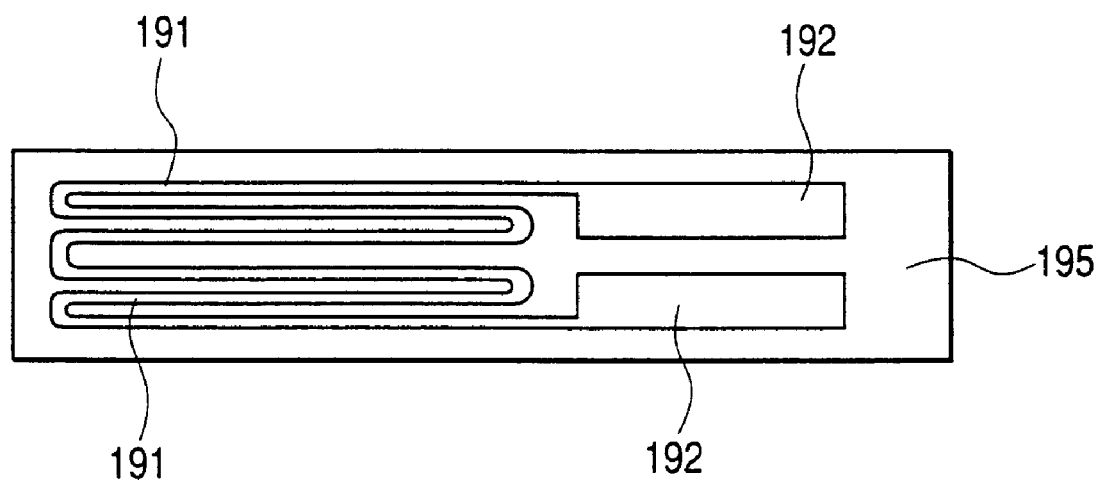
FIG. 5 is a plan view showing third configurations of the heat generator and the heater lead according to the first embodiment.
Figure 6:
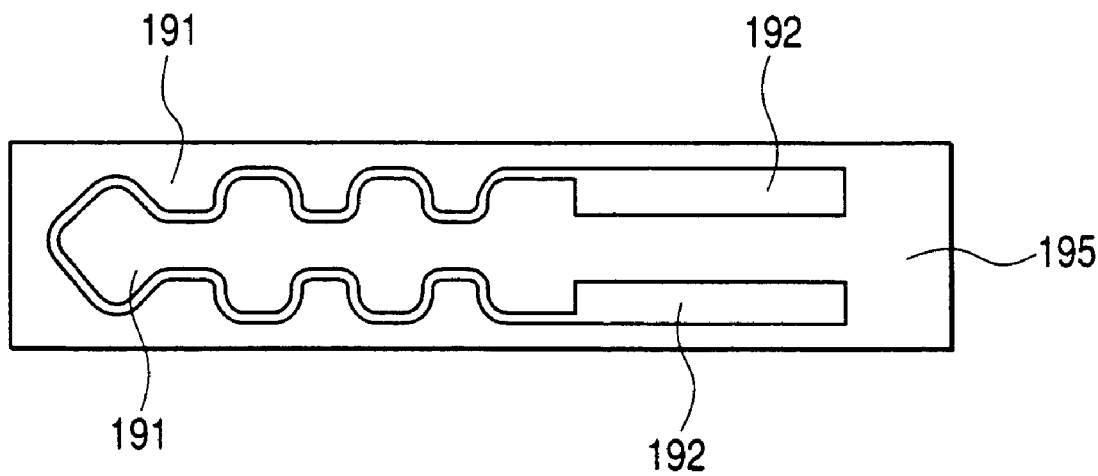
FIG. 6 is a plan view showing fourth configurations of the heat generator and the heater lead according to the first embodiment.

Moreover, also in a multilayer gas sensing element 1 equipped with each of heat generators 191 shown in FIGS. 4 to 6 which has a configuration other than the configuration shown in FIG. 3, if the ratio of the electrical resistance values of the heat generator 191 and the heater lead 192 is set to satisfy 1.5≦RH/RL, similar effects are obtainable.

Although a configuration shown in FIG. 4 is similar to that of FIG. 3, corner portions of the heat generator 191 are formed into a round shape, i.e., a curve configuration. FIG. 5 shows an example in which the heat generator 191 has a higher density, and FIG. 6 shows an example in which the heat generator 191 is formed into a corrugated configuration in cross directions.

Moreover, when the heat generator 191 and the heater lead 192, which have configurations shown in FIG. 3, are made of materials having the same composition while the thickness of the heat generator 191 is set at 40 µm and the thickness of the heater lead 192 is set at 60 µm, it is also possible that the electrical resistance value of the heat generator 191 is set at 1.5 Ω and the electrical resistance value of the heater lead 192 is set at 0.5 Ω. This can also provide the effects similar to those of the above-described embodiment.

Second Embodiment

This embodiment relates to the evaluation of the performance of the multilayer gas sensing element according to the first embodiment. That is, a multilayer gas sensing element was produced which provides RH/RL=10 satisfying a condition that RH is sufficiently high, and the detection error of this multilayer gas sensing element is set at 1, while the detection errors of other multilayer gas sensing elements having difference RH/RL were measured and shown in FIG. 7.

A description will be given hereinbelow of a detection error measuring method. Gas sensing elements having different RH/RL were prepared and exposed to a measured gas containing 100 ppm of NO and the temperature of the measured gas was changed from 30° C. to 100° C. and the detection error of the NOx concentration was measured. The temperature of the detecting portion of the gas sensing element was maintained to be a constant value in such a manner as to change a voltage to be applied to the heater. In this measurement, the voltage to be applied to the heater varies in accordance with the temperature of the measured gas, and the quantity of heat generation of the heater lead also varies and, hence, the influence of the leakage current on the error is estimable.

Figure 7:
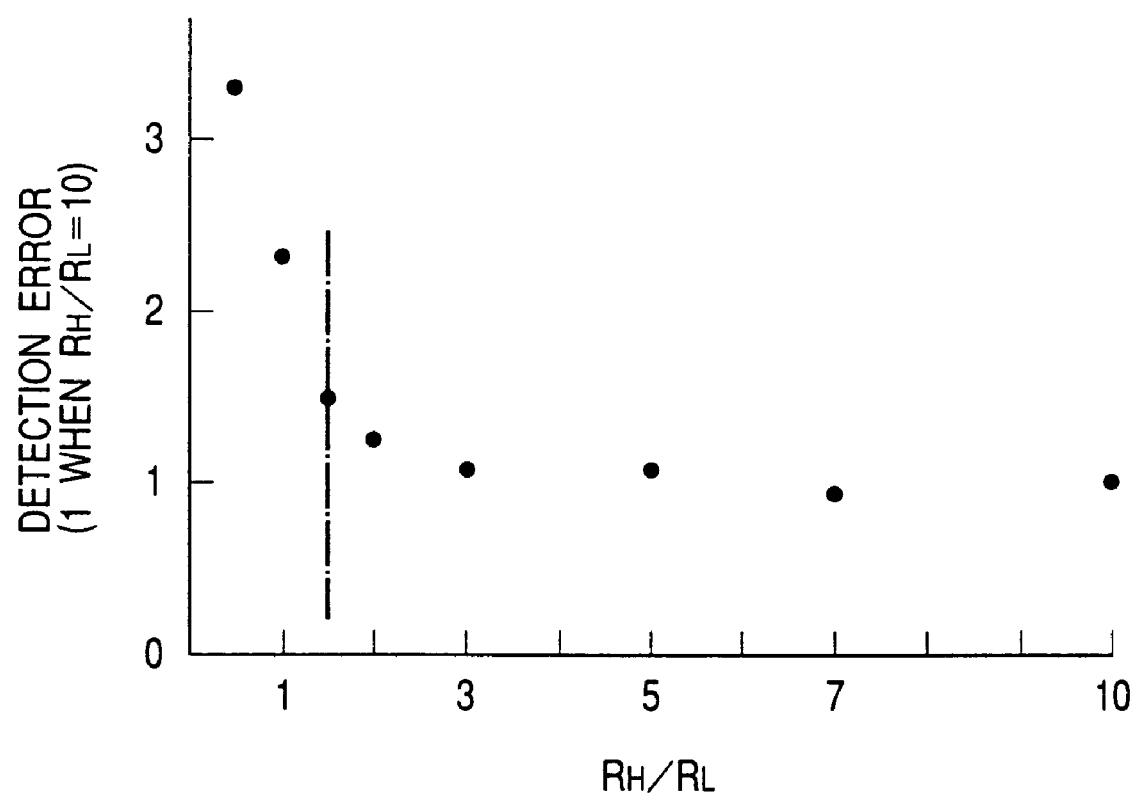
FIG. 7 is a graphic illustration of the relationship between PH/RL and detection error according to a second embodiment of the present invention.

From FIG. 7, the detection error increase as RH/RL decreases, and it was found that, for achieving a high detection accuracy, it is required that RH/RL be equal to or more than 2 (preferably, equal to or more than 3).

Third Embodiment

Figure 8A:
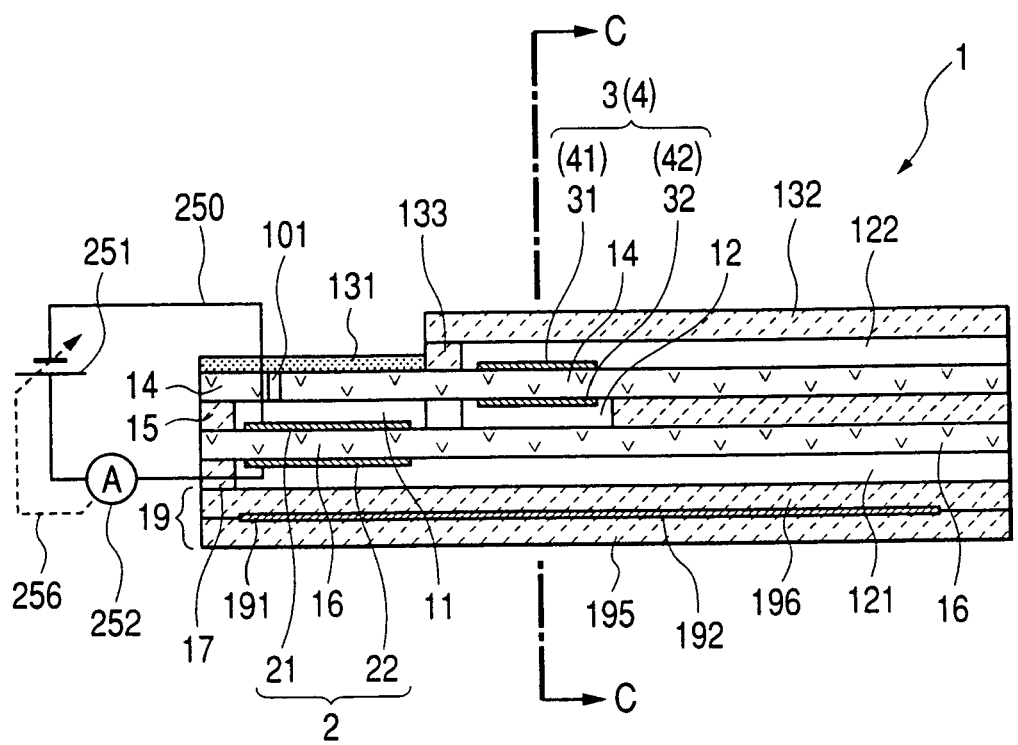
FIG. 8A is a longitudinal cross-sectional view showing a multilayer gas sensing element according to a third embodiment of the present invention, which is designed to be controlled on the basis of an applied voltage to an oxygen pump cell and a current flowing through the oxygen pump cell.
Figure 8B:
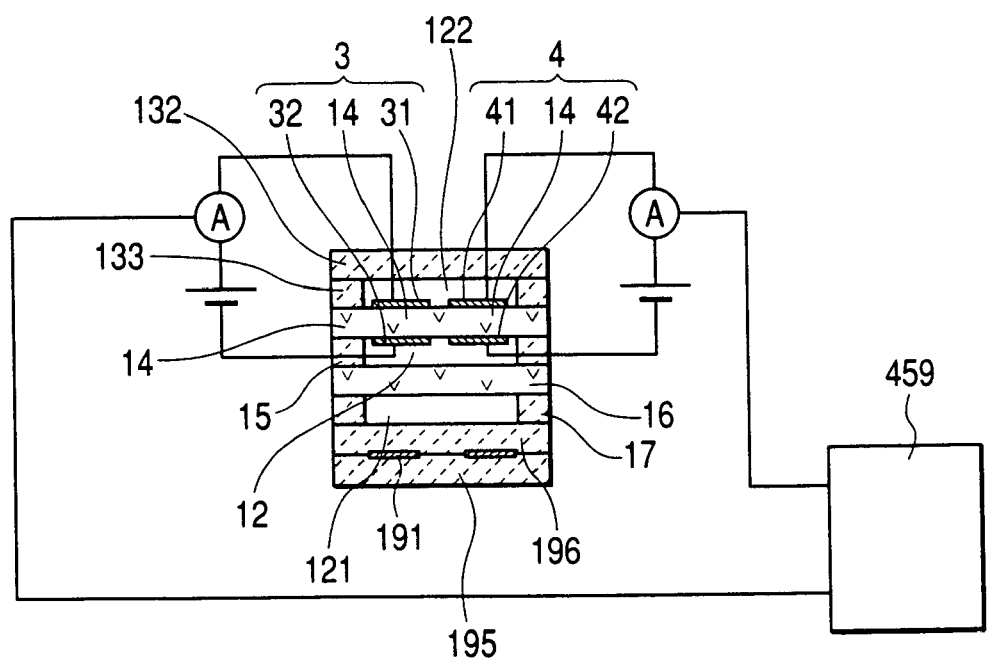
FIG. 8B is a transverse cross-sectional view taken along an arrow-indicated line C-C of FIG. 8A.

FIGS. 8A and 8B are illustrations of a multilayer gas sensing element according to a third embodiment of the present invention. As shown in FIGS. 8A and 8B, in the multilayer gas sensing element 1 according to this embodiment, the parts configuration is substantially the same as that of the element 1 according to the first embodiment but the circuit arrangement thereof is different from that in the first embodiment.

That is, a pump circuit 250 includes a power source 251 and an ammeter 252, and a voltage is applied in accordance with an oxygen concentration on the basis of the relationship between a voltage applied to the oxygen pump cell 2 and a current flowing through the oxygen pump cell 2, which is obtained in advance, so that an oxygen pump current agrees with a limiting current.

Thus, the oxygen concentrations in the first measured gas chamber 11 and the second measured gas chamber 12 can be controlled to a predetermined low concentration.

In a case in which the oxygen concentrations in the first and second measured gas chambers 11 and 12 are controlled in this way, as compared with the control based on the oxygen monitor cell according to the first embodiment, the oxygen concentration in the second measured gas chamber 12 tends to vary and, hence, the NOx detection accuracy degrades if a current flowing between the electrodes 41 and 42 of the sensor cell 4 is directly used as a sensor signal.

For this reason, the difference between a current flowing between the electrodes 41 and 42 of the sensor cell 4 and a current flowing between the electrodes 31 and 32 of the oxygen monitor cell is detected in a current difference detecting circuit 459 and this difference is used as a sensor signal, thereby reducing the influence of the oxygen concentration variation in the second measured gas chamber 12 to provide a sensor cell output representative of a more accurate NOx concentration without depending upon an oxygen concentration of the measured gas.

Fourth Embodiment

Figure 9:
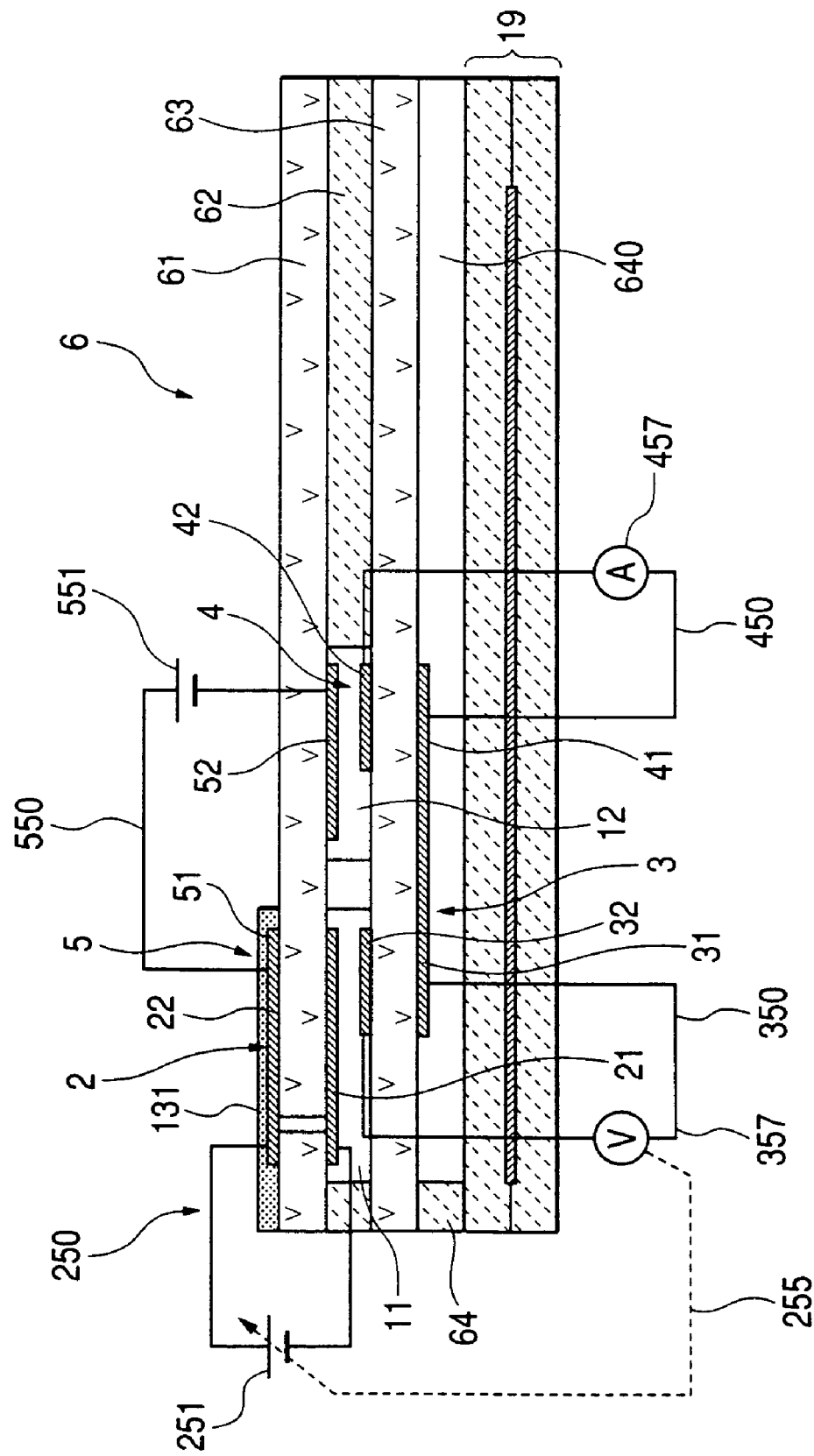
FIG. 9 is a longitudinal cross-sectional view showing a multilayer gas sensing element including first and second oxygen pump cells according to a fourth embodiment of the present invention.

FIG. 9 is an illustration of a multilayer gas sensing element according to a fourth embodiment of the present invention. As FIG. 9 shows, an multilayer gas sensing element 6 according to this embodiment is equipped with four cells including a second oxygen pump cell 5.

That is, the multilayer gas sensing element 6 according to this embodiment is made such that a spacer 64 for a reference gas chamber 640, a solid electrolyte plate 63 for the formation of an oxygen monitor cell 3 and a sensor cell 4, a spacer 62 for the formation of a first measured gas chamber 11 and a second measured gas chamber 12 and a solid electrolyte plate 61 for the formation of an oxygen pump cell 2 and a second oxygen pump cell 5 are built up on a heater 19 similar to that of the above-described first embodiment.

The oxygen pump cell 2 is composed of an electrode 21 confronting the first measured gas chamber 11 and an electrode 22 covered with a porous protective layer 131 and exposed to a measured gas in the exterior of the element 6, and is connected to a pump circuit 250 including a power source 251.

The monitor cell 3 is composed of an electrode 32 confronting the first measured gas chamber 11 and an electrode 31 confronting the reference gas chamber 640, and is connected to a circuit 350 including a voltmeter 357.

The sensor cell 4 is composed of an electrode 42 confronting the second measured gas chamber 12 and an electrode 41 confronting the reference gas chamber 640, and is connected to a circuit 450 including an ammeter 457. The electrodes 31 and 41 are integrated as one electrode.

Between the voltmeter 357 and the power source 251, a control circuit 255 is provided for controlling the power source 251 for the oxygen pump cell 2 on the basis of a voltage value detected by the voltmeter 357.

The second oxygen pump cell 5 is composed of an electrode 51 integrated with the electrode 22 of the first oxygen pump cell 2 and an electrode 52 exposed to the second measured gas chamber 12, and is connected to a circuit 550 including a power source 551.

Although in the first embodiment the oxygen concentration in the second measured gas chamber 12 is detected on the basis of a current flowing through the oxygen monitor cell 3, in this embodiment, it is detected on the basis of an electromotive force occurring between the electrodes 31 and 32 of the oxygen monitor cell 3.

Referring to FIG. 9, a description will be given hereinbelow of an example of operation in this case.

The electrode 32 of the oxygen monitor cell 3 confronts the first measured gas chamber 11, and the electrode 31 thereof faces the reference gas chamber 640 into which the atmospheric air is introduced. Between the electrodes 31 and 32, an electromotive force occurs according to the Nernst's equation due to the difference in oxygen concentration between the first measured gas chamber 11 and the reference gas chamber 640.

Since the oxygen concentration in the reference gas chamber 640 is constant, the electromotive force occurring between the electrodes 31 and 32 reflects the oxygen concentration in the first measured gas chamber 11. Therefore, if the voltage to be applied between the electrodes 21 and 22 of the oxygen pump cell 2 is controlled so that the electromotive force occurring between the electrodes 31 and 32 becomes a predetermined constant value (for example, 0.20V), the concentration of the oxygen flowing into the second measured gas chamber 12 can be controlled to be constant.

In addition, in this embodiment, the second oxygen pump cell 5 is provided to discharge, to the external, the oxygen flowing into the second measured gas chamber 12 without being discharged by the oxygen pump cell 2.

Accordingly, the oxygen concentration in the second measured gas chamber 12 reaches approximately zero and, hence, the sensor cell 4 can measure the NOx concentration with high accuracy.

The other configurations such as the heater 19 are similar to those in the first embodiment, and the effects similar thereto are obtainable.

Fifth Embodiment

Referring to FIGS. 10 to 15D, a description will be given hereinbelow of a gas sensing element according to a fifth embodiment of the present invention.

A gas sensing element 1 according to this embodiment is made up of heater 606 including a heater substrate 615, a heat generator 661 provided on the heater substrate 615 for generating heat when energized and heater terminals 6613 electrically connected through heater leads 6611 to the heat generator 661, a spacer 612 for a measured gas chamber into which a measured gas is introduced from the external, spacers 614 and 616 for a reference gas chamber into which a reference gas is introduced, and a solid electrolyte plate 611 for forming a monitor cell 603, a sensor cell 604 and a λ cell 605 each of which forms an electrochemical cell having a pair of electrodes to detect a specified gas concentration on the basis of a minute current stemming from oxygen ions and flowing between the pair of electrodes, with these components being built up into a multilayer configuration.

In addition, a leakage current conducting path is established in the middle of an electrical path between the aforesaid heater 606 and the aforesaid monitor cell 603, sensor cell 604 and λ cell 605 in order to lead a leakage current 619 from the heater 606 to the external.

In this embodiment, the leakage current conducting path is made utilizing pump leads 6211 and 6221 which will be mentioned later.

A detailed description will be given hereinbelow of the gas sensing element according to this embodiment.

The gas sensing element 1 according to this embodiment is used in a state incorporated into a gas sensor placed in an exhaust system of an engine of a vehicle for the purpose of the control of combustion of the engine. Moreover, this gas sensing element 1 is for measuring a NOx concentration of an exhaust gas, measuring an oxygen concentration thereof, and detecting a λ point (theoretical air fuel ratio point) of the engine.

Figure 10:
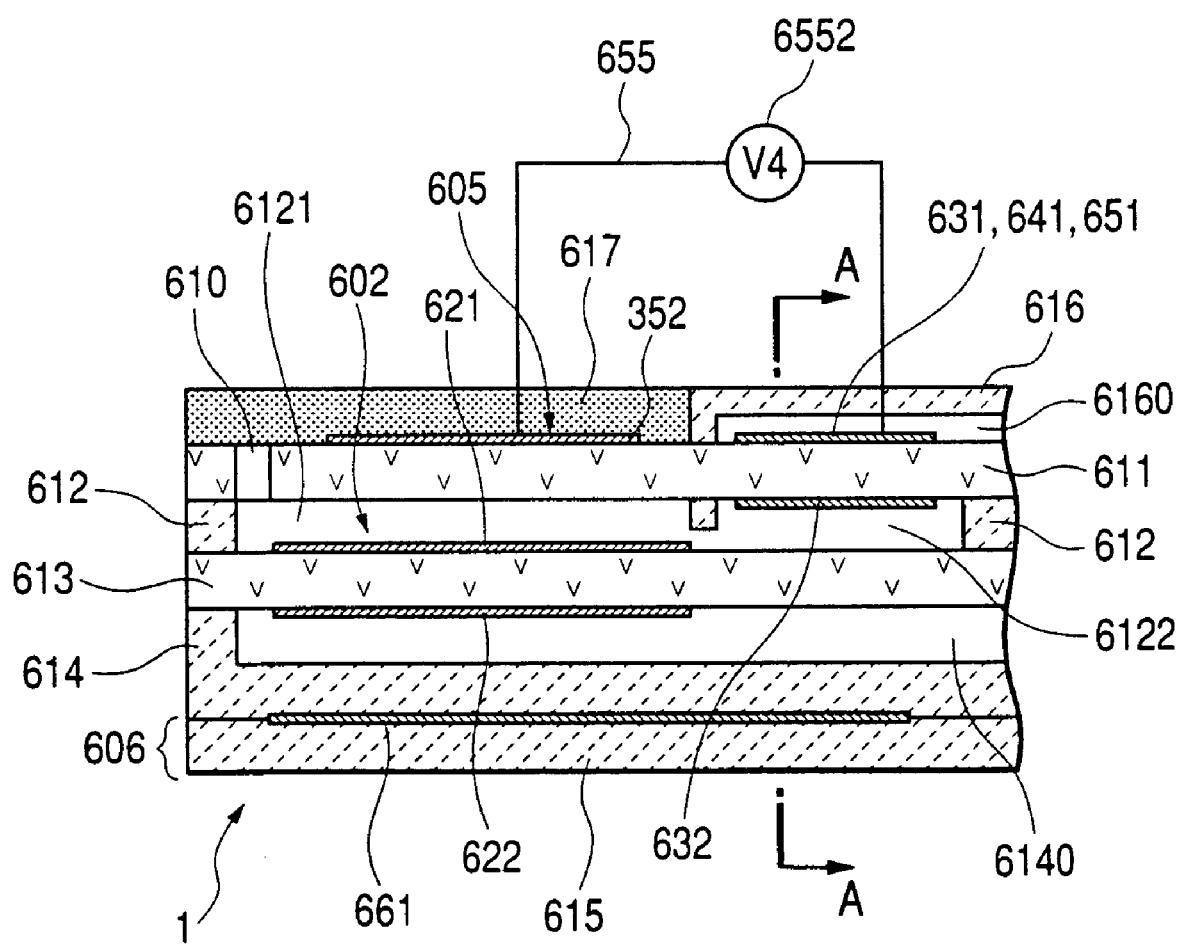
FIG. 10 is a longitudinal cross-sectional view showing an essential part of a gas sensing element according to a fifth embodiment of the present invention.

As FIG. 10 shows, in this embodiment, for the formation of the gas sensing element 1, the building-up is made in the order of the heater 606, the spacer 614 for a first reference gas chamber 6140, a pump cell solid electrolyte plate 613, the spacer 612 for the formation of first and second measured gas chambers 6121 and 6122, a solid electrolyte plate 611, the spacer 616 for the formation of a second reference gas chamber 6160 and a diffusion resistance layer 617 from the lower side of the illustration.

An exhaust gas is introduced into the first and second measured gas chambers 6121 and 6122 from the external, while atmospheric air is introduced into the first and second reference gas chambers 6140 and 6160.

Thus, the gas sensing element 1 comprises the first and second measured gas chambers 6121 and 6122, the first and second reference gas chambers 6140 and 6160, the pump cell 602 for pumping oxygen with respect to the first measured gas chamber 6121, the monitor cell 603 for monitoring an oxygen concentration in the second measured gas chamber 6122, the sensor cell 604 for detecting a NOx concentration in the second measured gas chamber 6122, and the λ cell 605 for detecting a λ point on the basis of an oxygen concentration of a measured gas in the exterior of the gas sensing element 1.

The first and second measured gas chambers 6121 and 6122 are formed among the solid electrolyte 611, the pump cell solid electrolyte plate 613 and the spacer 612, and the first measured gas chamber 6121 communicates with the external through an introduction hole 610 made in the solid electrolyte plate 611. A diffusion passage 6120 is provided between the first measured gas chamber 6121 and the second measured gas chamber 6122.

Moreover, the gas sensing element 1 according to this embodiment comprises a diffusion resistance layer 617 made to cover the introduction hole 610 of the solid electrolyte plate 611, and the spacer 616 for the formation of the second reference gas chamber 6160 is located in a state adjacent to the diffusion resistance layer 617.

Still moreover, the first reference gas chamber 6140 is defined by the pump cell solid electrolyte plate 613, the spacer 614 and the heater 606.

The heater 606 is composed of the heater substrate 615 and the heat generator 661 placed on the heater substrate 615.

The solid electrolyte plate 611 and the pump cell solid electrolyte 613 are made of zirconia ceramics, while the heater substrate 615, the spacers 614, 612, 616 and the diffusion resistance layer 617 are made of insulating alumina ceramics.

Figure 11:
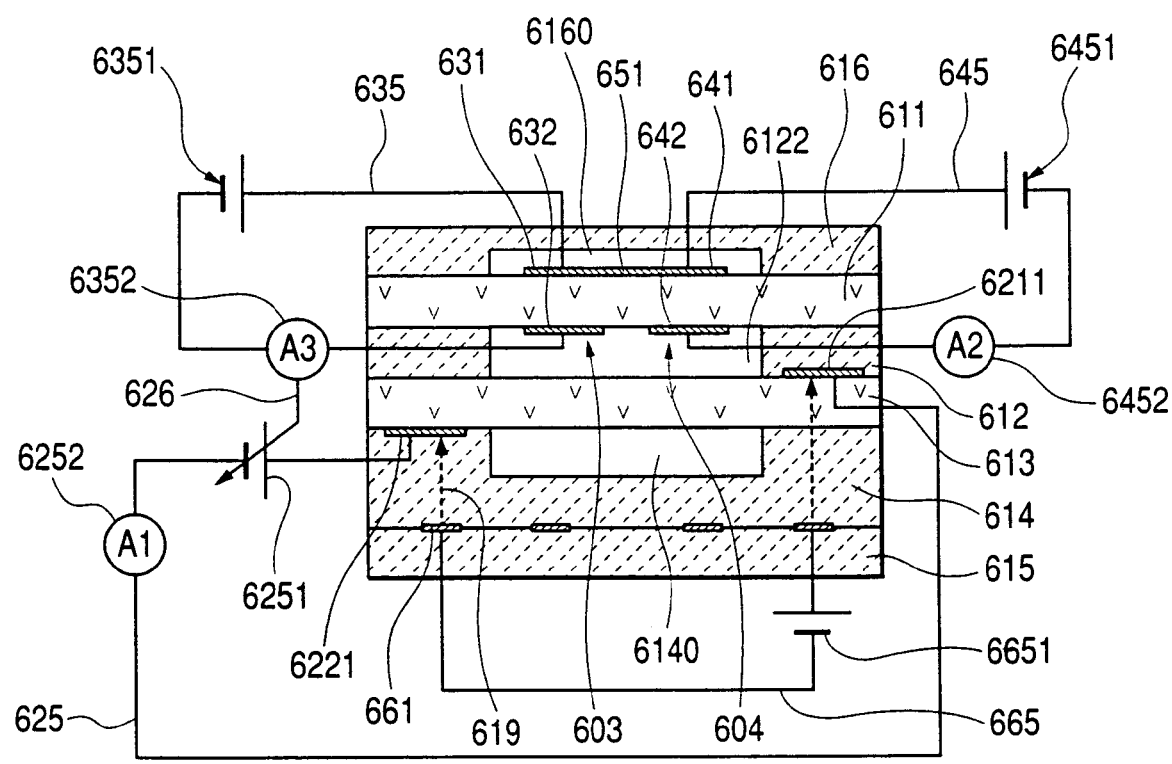
FIG. 11 is a cross-sectional view taken along a line A-A of FIG. 10.

As shown in FIGS. 10 and 11, the aforesaid pump cell 602 is composed of a first pump electrode 621 provided on the pump cell electrolyte plate 613 to confront the first measured gas chamber 6121 and a second pump electrode 622 provided thereon to confront the first reference gas chamber 6140. Both the electrodes 621 and 622 is connected to a pump circuit 625 including a variable power source 6251 and an ammeter 6252.

The aforesaid monitor cell 603 is composed of a measured gas side electrode 632 provided on the solid electrolyte plate 611 to face the second measured gas chamber 6122 and a reference electrode 631 provided thereon to face the second reference gas chamber 6160. Both the electrodes 631 and 632 are connected to a monitor circuit 635 including a power source 6351 and an ammeter 6352.

Moreover, a feedback circuit 6255 from the ammeter 6352 to the power source 6251 is provided for the purpose of controlling the pump cell 602 through the use of the monitor cell 603.

The aforesaid sensor cell 604 is composed of a measured gas side electrode 642 provided on the solid electrolyte plate 611 to confront the second measured gas chamber 6122 and a reference electrode 641 provided thereon to confront the second reference gas chamber 6160. Both the electrodes 641 and 642 are connected to a sensor circuit 645 including a power source 6451 and an ammeter 6452.

As FIG. 10 shows, the λ cell 605 is provided between the solid electrolyte plate 611 and the diffusion resistance layer 617, and is composed of a measured gas side electrode 652 exposed through the diffusion resistance layer 617 to a measured gas in the exterior of the sensing element 1 and a reference electrode 651 confronting the second reference gas chamber 6160. Both the electrodes 651 and 652 are connected to a λ cell circuit 655 including a voltmeter 6552.

Moreover, the heat generator 661 of the heater 606 is connected through heater leads or terminals, which will be mentioned later, to a heater circuit 665 including a power source 6651.

Figure 14A:
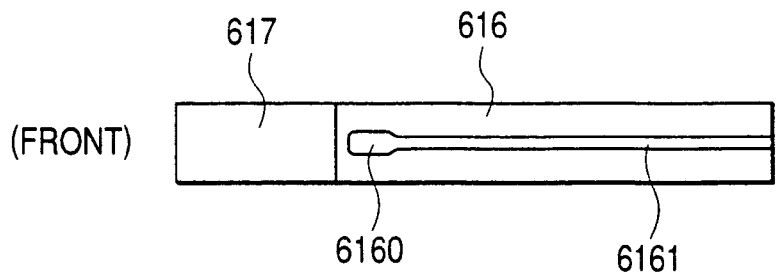
FIG. 14A is a plan view showing a diffusion resistance layer and a spacer according to the fifth embodiment.
Figure 14B:
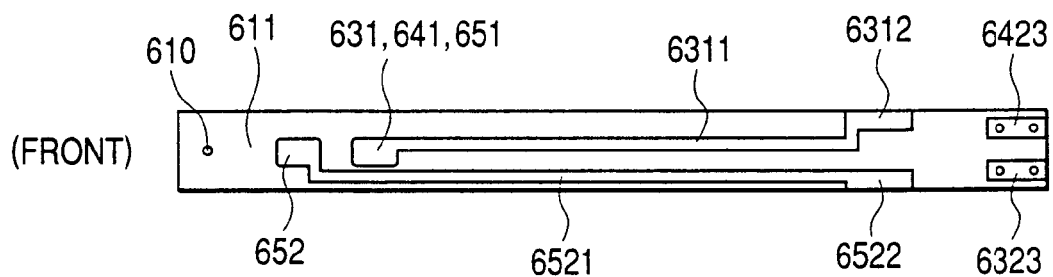
FIG. 14B is a plan view showing a front side of a pump cell solid electrolyte plate according to the fifth embodiment.

The reference electrodes 631, 641 and 651 of the monitor cell 603, the sensor cell 604 and the λ cell 605 are formed integrally as a common electrode as shown in FIGS. 10 and 14B.

Still moreover, the power sources 6351 and 6451 produce a voltage of 0.4V, the variable power source 6251 produces a voltage of 0.3V to 0.5V, and the power source 6651 produces a voltage of 0 to 16V, with these voltages being applied to the cells 602, 603, 604 and the heat generator 661.

Figure 13A:
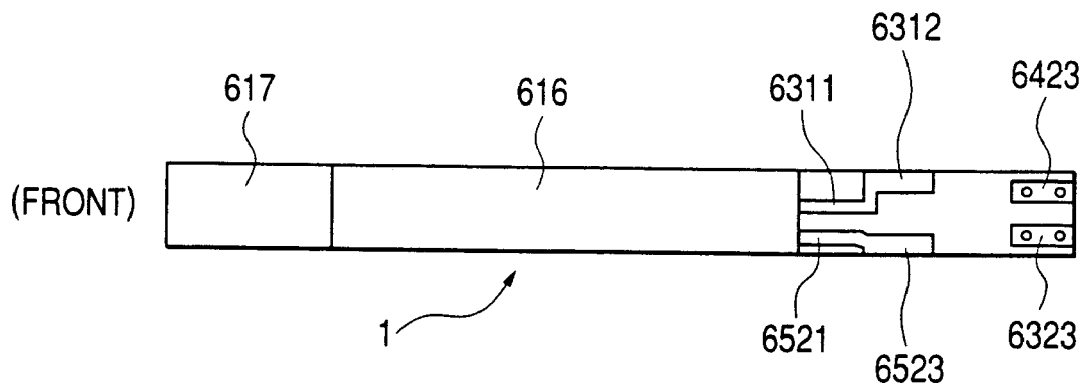
FIG. 13A is a plan view showing a diffusion resistance layer side of the gas sensing element according to the fifth embodiment.
Figure 13B:
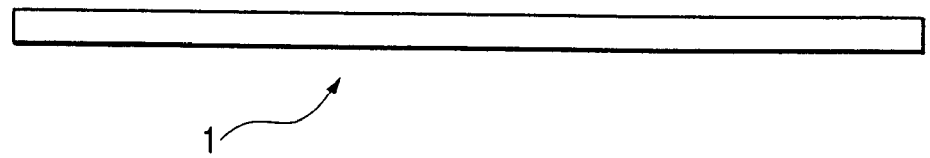
FIG. 13B is a side elevational view showing the gas sensing element according to the fifth embodiment.
Figure 13C:
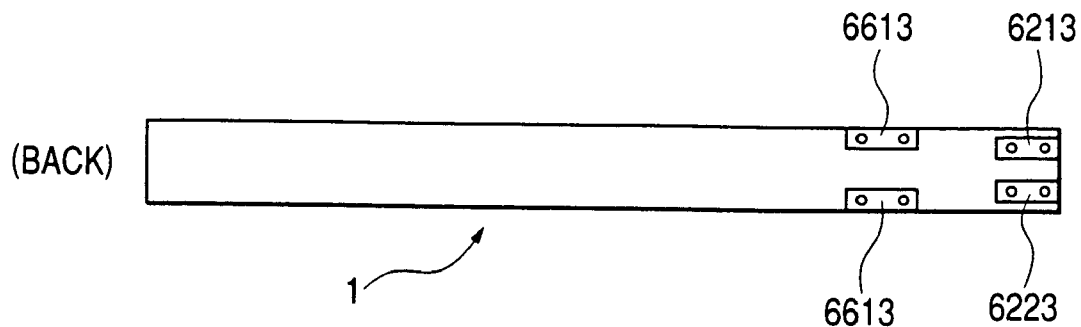
FIG. 13C is a plan view showing a heater side of the gas sensing element according to the fifth embodiment.

FIG. 13A is a plan view showing the gas sensing element 1 when viewed from the diffusion resistance layer 617 and spacer 616 side, FIG. 13B is a side elevational view showing the gas sensing element, and FIG. 13C is a plan view showing the gas sensing element 1 when viewed from the heater 606 side.

On the diffusion resistance layer 617 side and the space 616 side, terminals 6312, 6523, 6423 and 6323 are exposed, and on the heater 606 side, terminals 6613, 6213 and 6223 are exposed to the exterior of the gas sensing element 1. The connections of the heater 606, the pump cell 602, the monitor cell 603, the sensor cell 604 and the λ cell 605 to the circuits 665, 625, 635, 645 and 655 are established through the use of these terminals.

FIGS. 14A to 14D and 15A to 15D are plan views showing the solid electrolyte plate 611 and others constituting the gas sensing element 1, where (FRONT) designates a configuration when viewed from the diffusion resistance layer 617 and spacer 616 side and (BACK) denotes a configuration when viewed from the heater 606 side.

FIG. 14A shows the diffusion resistance layer 617 and the reference gas chamber spacer 616, and the spacer 616 includes an elliptical reference gas chamber 6160 and an introduction path 6161 for introducing atmospheric air from the external into the reference gas chamber 6160.

FIG. 14B shows a front side of the solid electrolyte plate 611, and shows the measured gas side electrode 652 of the λ cell 605 and a common electrode to be used as the reference electrodes 631, 641 and 651 of the monitor cell 603, the sensor cell 604 and the λ cell 605. Moreover, in the illustration, there appear a λ cell lead 6521 formed integrally with the measured gas side electrode 652, a terminal 6523, a common lead 6311 formed integrally with the common electrode and a terminal 6312. Further shown are terminals 6323 and 6423 connected through conductive through-holes to terminals 6322 and 6422 shown in FIG. 14C.

Figure 14C:
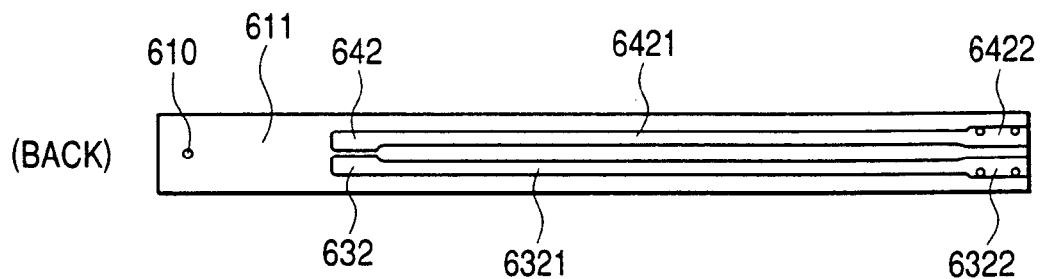
FIG. 14C is a plan view showing a back side of the pump cell solid electrolyte plate according to the fifth embodiment.

FIG. 14C shows a back side of the solid electrolyte plate 611, where there are the measured gas side electrodes 632 and 642 of the monitor cell 603 and the sensor cell 604. Further shown are a monitor cell lead 6321 and a sensor cell lead 6421 which are formed integrally with the measured gas side electrodes 632 and 642, respectively, and still further shown are terminals 6322 and 6422 which are also formed integrally therewith, respectively.

The terminals 6322 and 6422 are electrically connected through the conductive through holes to the terminals 6323 and 6423 provided on a surface exposed to the exterior of the gas sensing element 1 as shown in FIG. 13A.

Figure 14D:
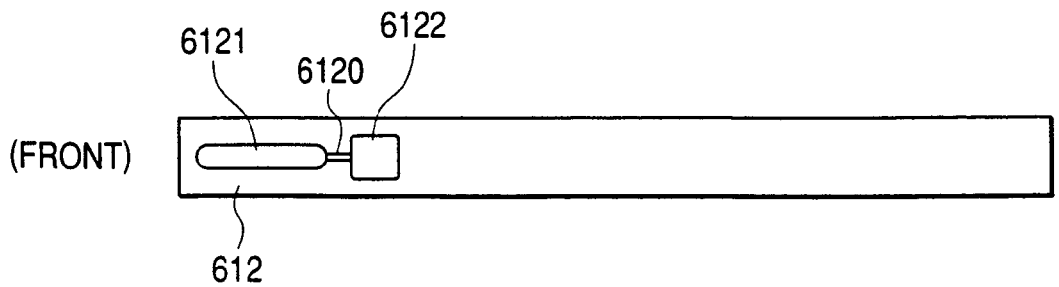
FIG. 14D is a plan view showing a spacer according to the fifth embodiment.

FIG. 14D shows a front side of the spacer 612, where there appear the first measured gas chamber 6121, the second measured gas chamber 6122 and the diffusion passage 6120 for making a communication therebetween.

Figure 15A:
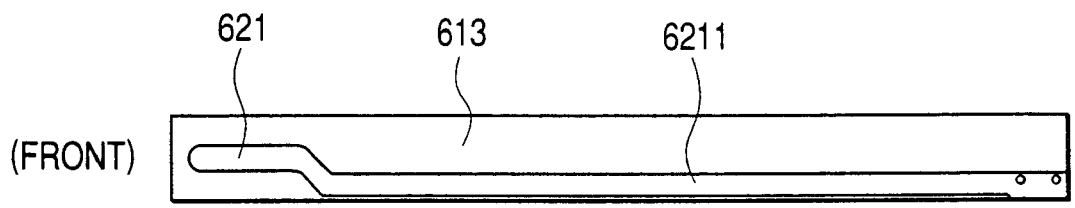
FIG. 15A is a plan view showing a front side of a pump cell solid electrolyte plate according to the fifth embodiment.
Figure 15B:
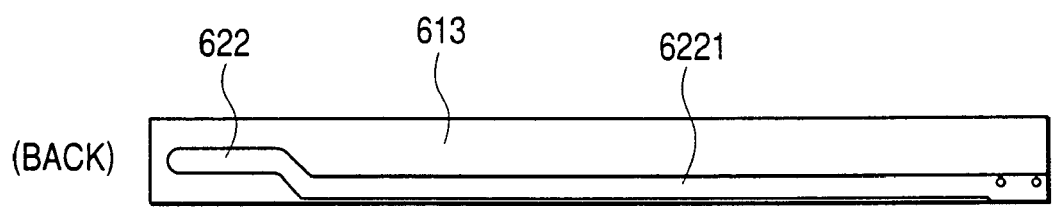
FIG. 15B is a plan view showing a back side of the pump cell solid electrolyte plate according to the fifth embodiment.

As shown in FIGS. 15A and 15B, the pump cell solid electrolyte plate 613 is equipped with the pump leads 6211 and 6221 formed integrally with the first and second pump electrodes 621 and 622. The pump leads 6211 and 6221 are located in first and second boundary surfaces 6105 and 6106, formed between the spacer 614 and the pump cell solid electrolyte plate 613 and between the solid electrolyte plate 613 and the spacer 612, at edge sides of the solid electrolyte plate 613 as seen from FIGS. 11 and 12.

A description will be given hereinbelow of the above-mentioned pump lead 6211.

Figure 12:
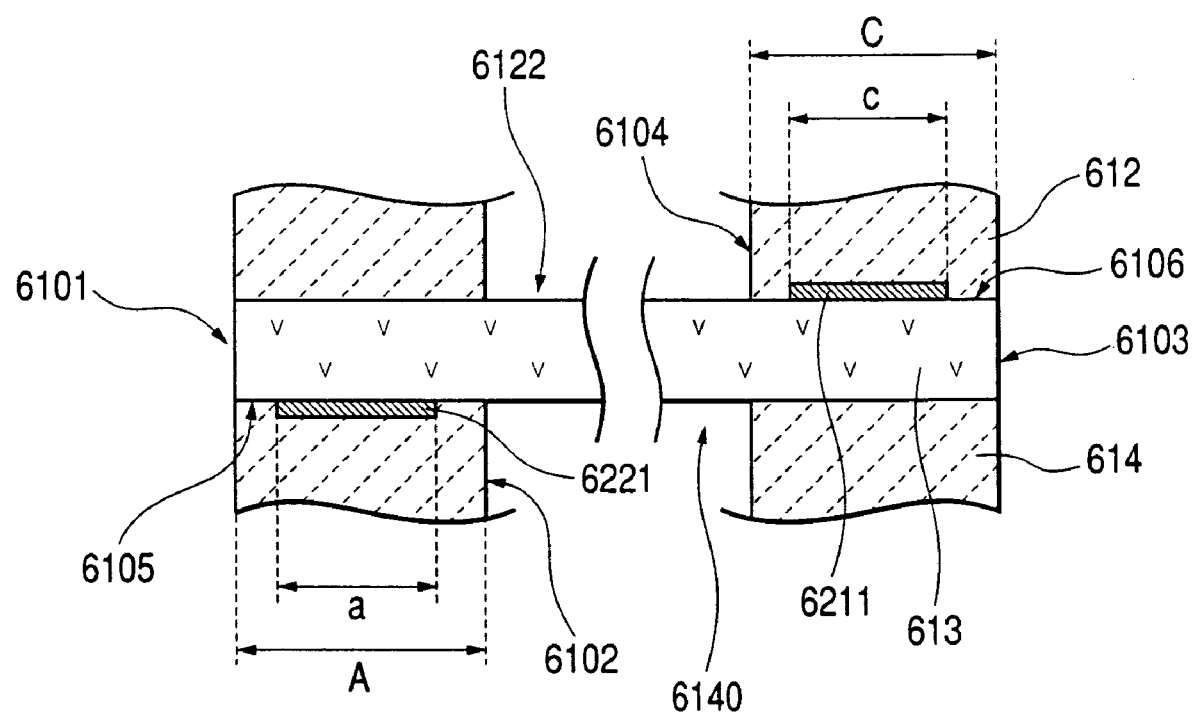
FIG. 12 is an illustration useful for explaining widths of pump leads and widths of first and second boundary surfaces according to the fifth embodiment.

As shown in FIGS. 11 and 12, the first boundary surface 6105 is formed between an outer surface 6101 of the gas sensing element 1 and an inner surface 6102 of the reference gas chamber 6140, which are formed along width directions perpendicular to a longitudinal (lengthwise) direction of the gas sensing element 1, and between the spacer 614 and the pump cell solid electrolyte plate 613. On the other hand, the second boundary surface 6106 is formed between an outer surface 6103 different from the outer surface 6101 and an inner surface 6104 of the measured gas chamber 6122 and between the spacer 612 and the pump cell solid electrolyte plate 613.

When a minimum width of the first boundary surface 6105 is taken to be A and a maximum width of the pump lead 6221 along the cross direction is taken as a, the relationship of $0.1 \leq a/A$ is satisfied.

Moreover, a minimum width of the second boundary surface 6106 is taken as C and a maximum width of the pump lead 6211 along the cross direction is taken as c, the relationship of $0.1 \leq c/C$ is satisfied.

In addition, the pump leads 6211 and 6221 are electrically connected through conductive through holes to the terminals 6213 and 6223 of the heater substrate 615 exposed to the exterior of the gas sensing element 1.

Figure 15C:
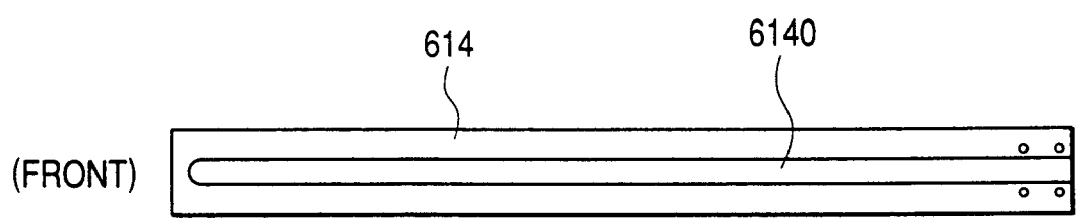
FIG. 15C is a plan view showing a spacer according to the fifth embodiment.

FIG. 15C shows a front side of the spacer 614, where there is the reference gas chamber 6140.

Figure 15D:
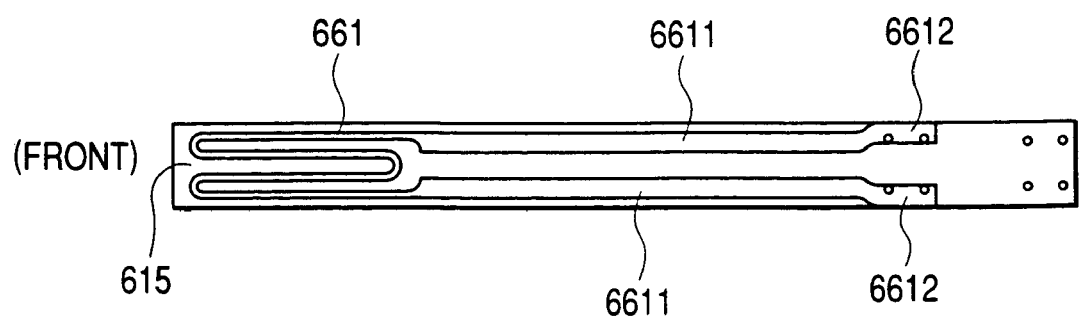
FIG. 15D is a plan view showing a heater substrate according to the fifth embodiment.

FIG. 15D shows front side of the heater 615, where there are the heat generator 661, the heater leads 6611 integrated with the heat generator 661 and the terminals 6612 integrated with the heat generator 661. The terminals 6612 are electrically connected through conductive through holes to the terminals 6613, provided on a surface exposed to the exterior of the gas sensing element 1, on the back side of the heater substrate 615 as shown in FIG. 13C.

In the gas sensing element 1, as shown in FIG. 11, the leakage currents 619 pass through the spacer 614, the pump cell solid electrolyte plate 613, the spacer 612 and the solid electrolyte plate 611 and are directed to the monitor cell 603, the sensor cell 604 and the λ cell 605 each of which forms an electrochemical cell.

In the gas sensing element 1 according to this embodiment, since, as the positional relationship, the pump leads 6211 and 6221 are placed to cross the electrical paths between the heater 606 and the above-mentioned electrochemical cells. Therefore, the pump leads 6211 and 6221 of the pump cell 602 function as a leakage current conducting path to lead the leakage currents from the heater 606 to portions other than the electrochemical cells.

The first pump electrode 621 and the measured gas side electrode 632 are a Pt—Au electrode inactive for NOx. The content of Au is 3 wt %. The measured gas side electrode 642 is a Pt—Rh electrode active with respect to NOx. Each of the other electrodes 622, 631, 641, 651 and 652 is a Pt electrode.

Figure 27:
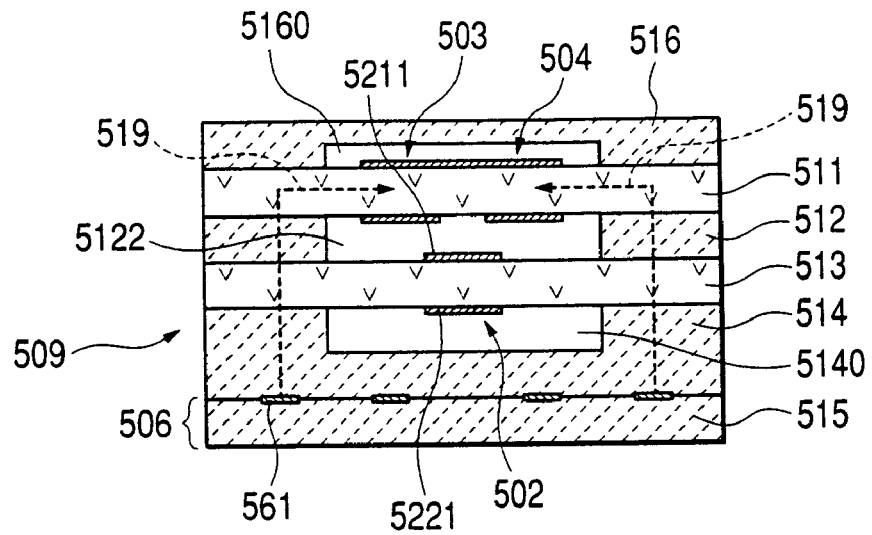
FIG. 27 is a transverse cross-sectional view showing a gas sensing element having a conventional construction.
Figure 28A:
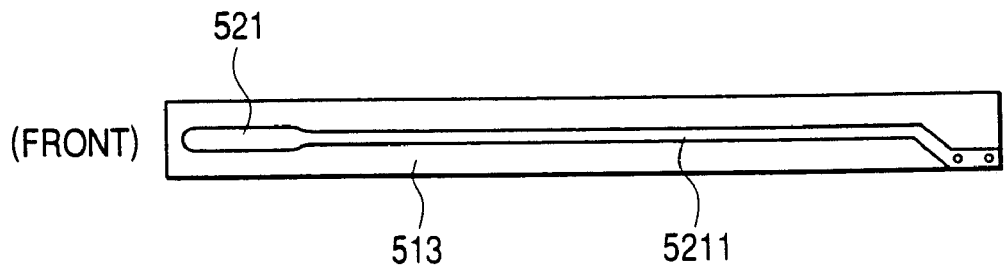
FIG. 28A is a plan view showing a front side of a pump cell solid electrolyte plate in a conventional gas sensing element.
Figure 28B:
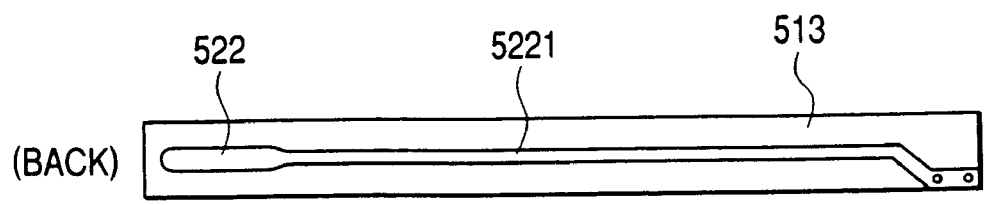
FIG. 28B is a plan view showing a back side of the pump cell solid electrolyte plate in the conventional gas sensing element.

The gas sensing element 1 according to this embodiment was compared in performance with a conventional gas sensing element. FIGS. 27, 28A and 28B are illustrations of the conventional gas sensing element, generally designated at reference numeral 509.

Although the longitudinal cross-sectional view of the conventional gas sensing element is similar to that of this embodiment shown in FIG. 10, the cross section taken along the line A-A is as shown in FIG. 27. The front and back sides of the pump cell 513 are shown in FIGS. 28A and 28B. As shown in the illustrations, in the conventional gas sensing element 509, the pump leads 5211 and 5221 are located at central portions of the pump cell solid electrolyte plate 513.

For this reason, as shown in FIG. 27, the leakage currents 519 from the heater 506 pass through the spacer 514, the solid electrolyte plate 513, the spacer 512 and the solid electrolyte plate 511 and then enter the monitor cell 503, the sensor cell 504 and a λ cell (not shown).

The temperature dependency of the offset current was measured with respect to the sensor cell 504 of the conventional gas sensing element 509 and the sensor cell 604 of the gas sensing element 1 according to this embodiment. FIG. 16 shows the measurement results.

In this case, the offset current signifies a current value in the sensor cell 604 in a case in which a NOx concentration of a measured gas is zero. Although an oxygen ionic current should not flow in the sensor cell 604 when the NOx concentration is zero, in fact a given current flows due to the residual oxygen in the second measured gas chamber 6122.

In addition, the electrical resistance in the leakage current path falls with an increase in temperature and, hence, it is considered that a larger leakage current flows into the sensor cell 604.

Therefore, in the case of the conventional gas sensing element 509 having a structure in which the leakage current flows thereinto, the offset current increases with the temperature of the element 509.

On the other hand, in the case of the gas sensing element 1 according to this embodiment, since a leakage current flows through the pump leads 6211 and 6221, the offset current value hardly varies even if the element temperature rises.

Thus, in the gas sensing element 1 according to this embodiment, the pump leads 6211 and 6221 acting as a leakage current conducting path are provided in the first and second boundary 6105 and 6106 forming a leakage current path between the heater 606 and the monitor cell 603, the sensor cell 604 and the λ cell 605 each of which is an electrochemical cell.

Therefore, a leakage current is directed to the pump leads 6211 and 6221 establishing a leakage current conducting path and does not reach the monitor cell 603, the sensor cell 604 and the λ cell 605 each of which is an electrochemical cell.

Still additionally, in the gas sensing element 1 according to this embodiment, because of the employment of the pump leads 6211 and 6221 as a leakage current path, a minimum specification alteration from the conventional construction is feasible, which can reduce the number of parts accordingly as compared with a case of the employment of separate parts. This is advantageous in manufacturing cost or the like.

Accordingly, this embodiment can provide a gas sensing element whose measurement accuracy hardly drops due to a leakage current from the heater section.

Sixth Embodiment

Figure 17:
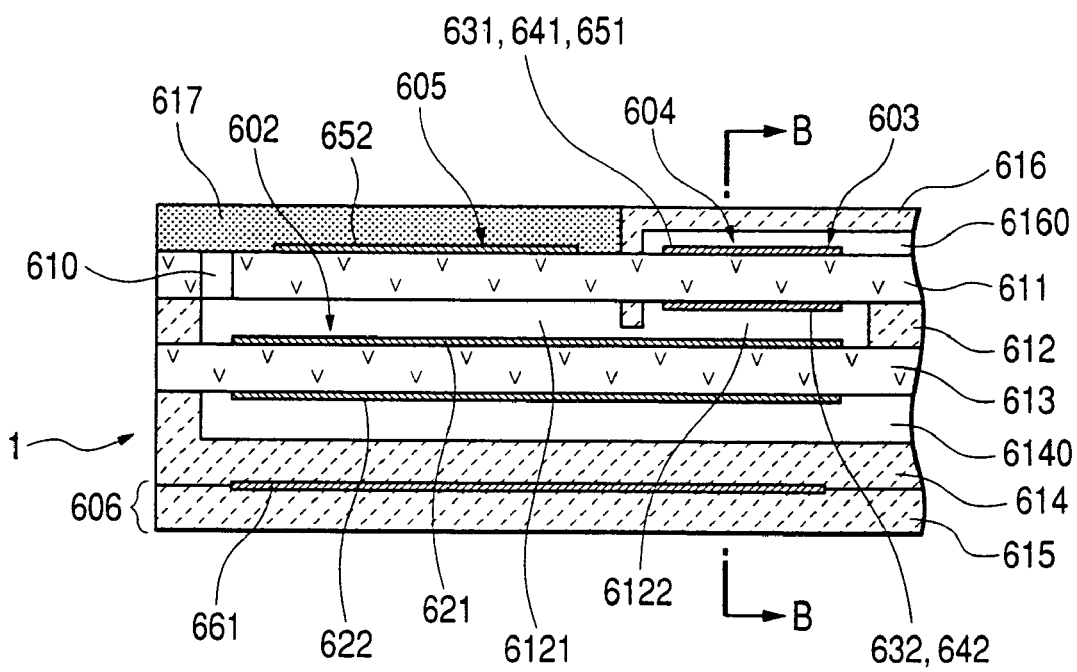
FIG. 17 is a longitudinal cross-sectional view showing an essential part of a gas sensing element having pump electrodes extending to positions of a sensor cell and a monitor cell according to a sixth embodiment of the present invention.
Figure 18:
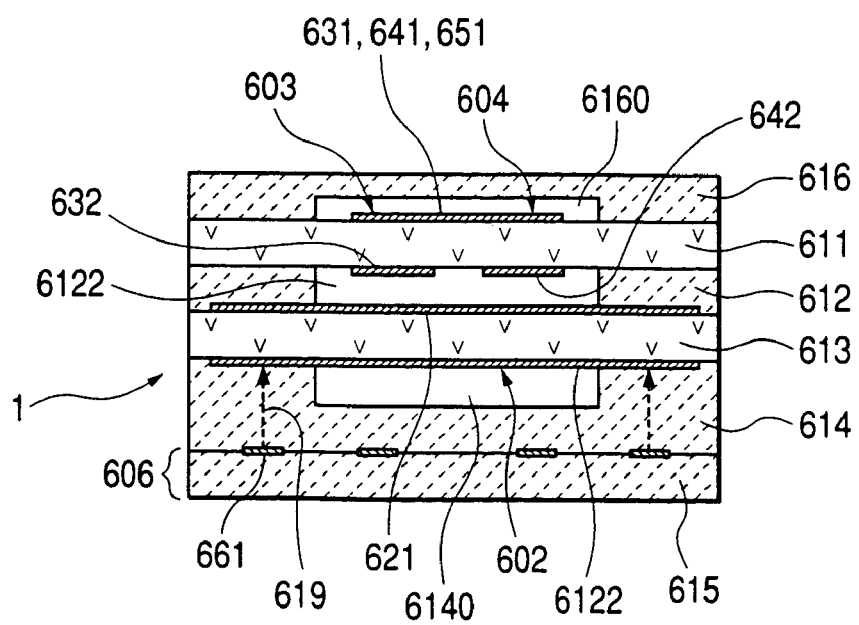
FIG. 18 is a cross-sectional view taken along a line B-B of FIG. 17.
Figure 19:
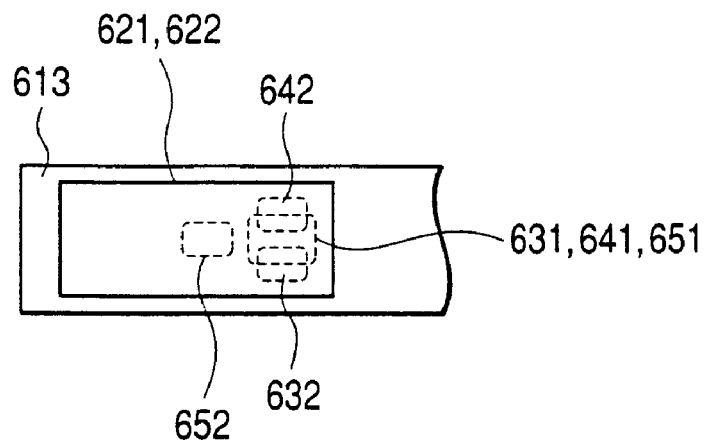
FIG. 19 is a longitudinal cross-sectional view showing an essential part of a gas sensing element having a conductive layer according to the sixth embodiment.

Referring to FIGS. 17 and 18, a description will be given hereinbelow of a gas sensing element 1 according to a sixth embodiment of the present invention. As shown in FIGS. 17 and 18, in the gas sensing element 1 according to this embodiment, pump electrodes 621 and 622 constituting a pump cell 602 are formed to extend to the positions of the sensor cell 604 and the monitor cell 603 for covering electrode projection planes made by projecting the electrodes 631, 632, 641, 642, 651 and 652 of the monitor cell 603, the sensor cell 604 and the λ cell 605 to the pump cell solid electrolyte plate 613 as shown in FIG. 19 (the external shapes of the respective electrodes are indicated by broken lines in FIG. 19 and the portions indicated by the broken lines form the electrode projection planes). With this construction, the pump electrodes 621 and 622 function as a leakage current conducting path to put out a leakage current 619. The other components are similar to those in the fifth embodiment.

In the gas sensing element 1 according to this embodiment, since the pump electrodes 621 and 622 are also used as the leakage current conducting path, a minimum specification alteration from the conventional construction is feasible, which can reduce the number of parts accordingly as compared with a case of the employment of separate parts. This is advantageous in manufacturing cost or the like. The other effects of this embodiment are similar to those of the fifth embodiment.

Seventh Embodiment

Figure 20:
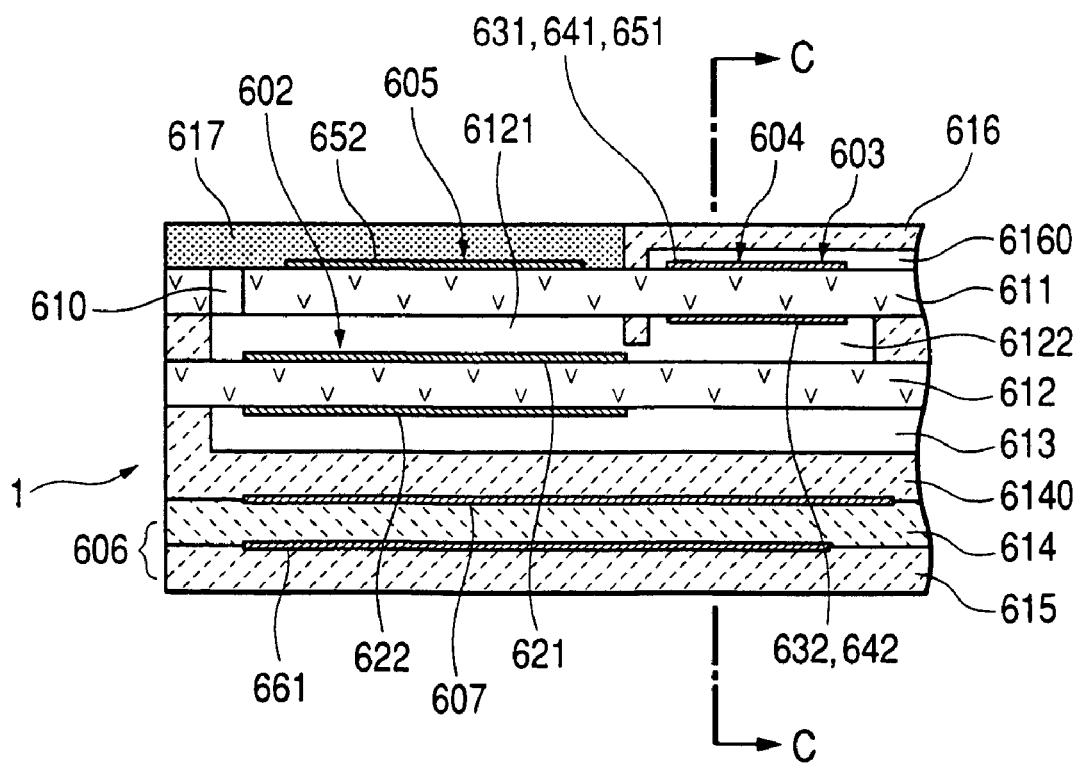
FIG. 20 illustratively shows a state in which electrodes are projected onto a pump cell solid electrolyte plate in a seventh embodiment of the present invention.
Figure 21:
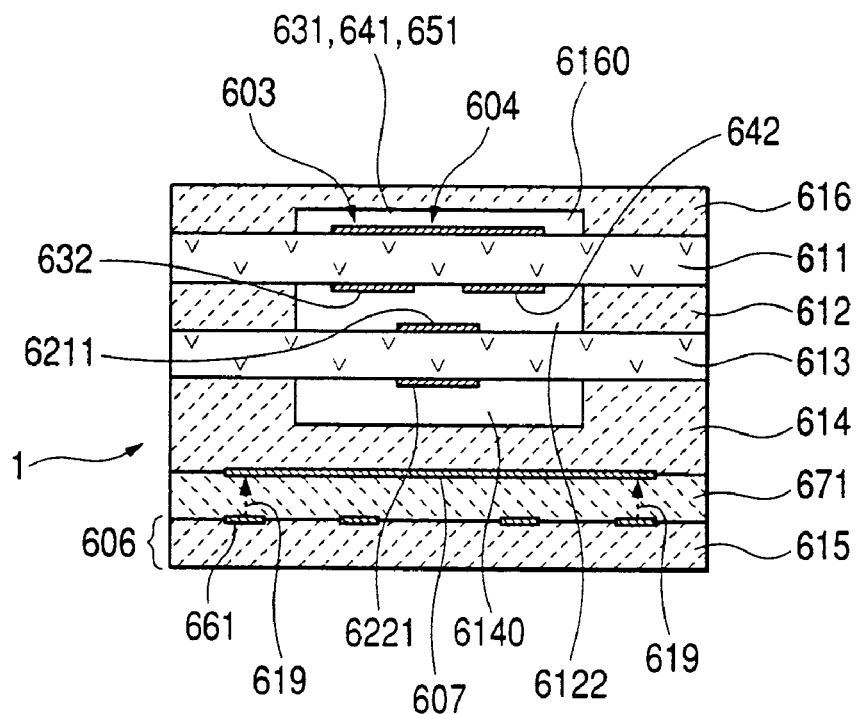
FIG. 21 is a cross-sectional view taken along a line C-C of FIG. 20.

Referring to FIGS. 20 and 21, a description will be given hereinbelow of a gas sensing element 1 according to a seventh embodiment of the present invention. As shown in FIGS. 20 and 21, in the gas sensing element 1 according to this embodiment, a conductive layer 607 is placed above the heater 606 in a state where an insulating plate 671 is interposed therebetween, and is used as a leakage current conducting path. This conductive layer 607 is formed to extend to at least the positions of the monitor cell 603 and the sensor cell 604 in a longitudinal direction of the gas sensing element 1.

Figure 22:
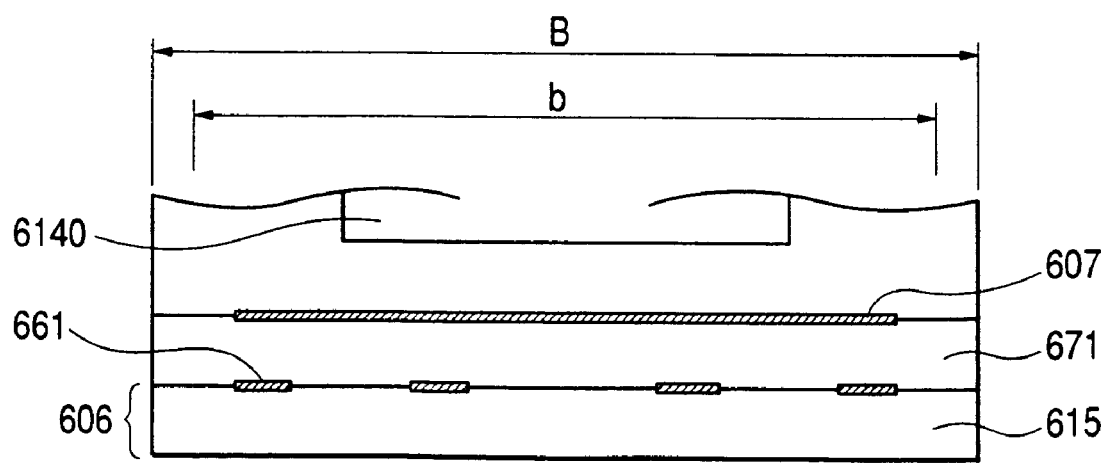
FIG. 22 is an illustration of the relationship between a width of a conductive layer and a width of an element according to the seventh embodiment.

Moreover, as shown in FIG. 22, when the width of the gas sensing element 1 in a cross direction perpendicular to the longitudinal direction of the gas sensing element 1 is taken as B and the width of the conductive layer 607 is taken as b, the relationship of $0.5 \leq b/B$ is satisfied.

The other construction is similar to that of the fifth embodiment.

In the gas sensing element 1 according to this embodiment, the conductive layer 607 acting as an electrical path for a leakage current is provided on the heater 606 side surface of the spacer 614 and, hence, a leakage current 619 flows through the conductive layer 607 so that it does not reach the monitor cell 603, the sensor cell 604 and the λ cell 605 each of which is an electrochemical cell.

The other effects of this embodiment are similar to those of the fifth embodiment.

Figure 23:
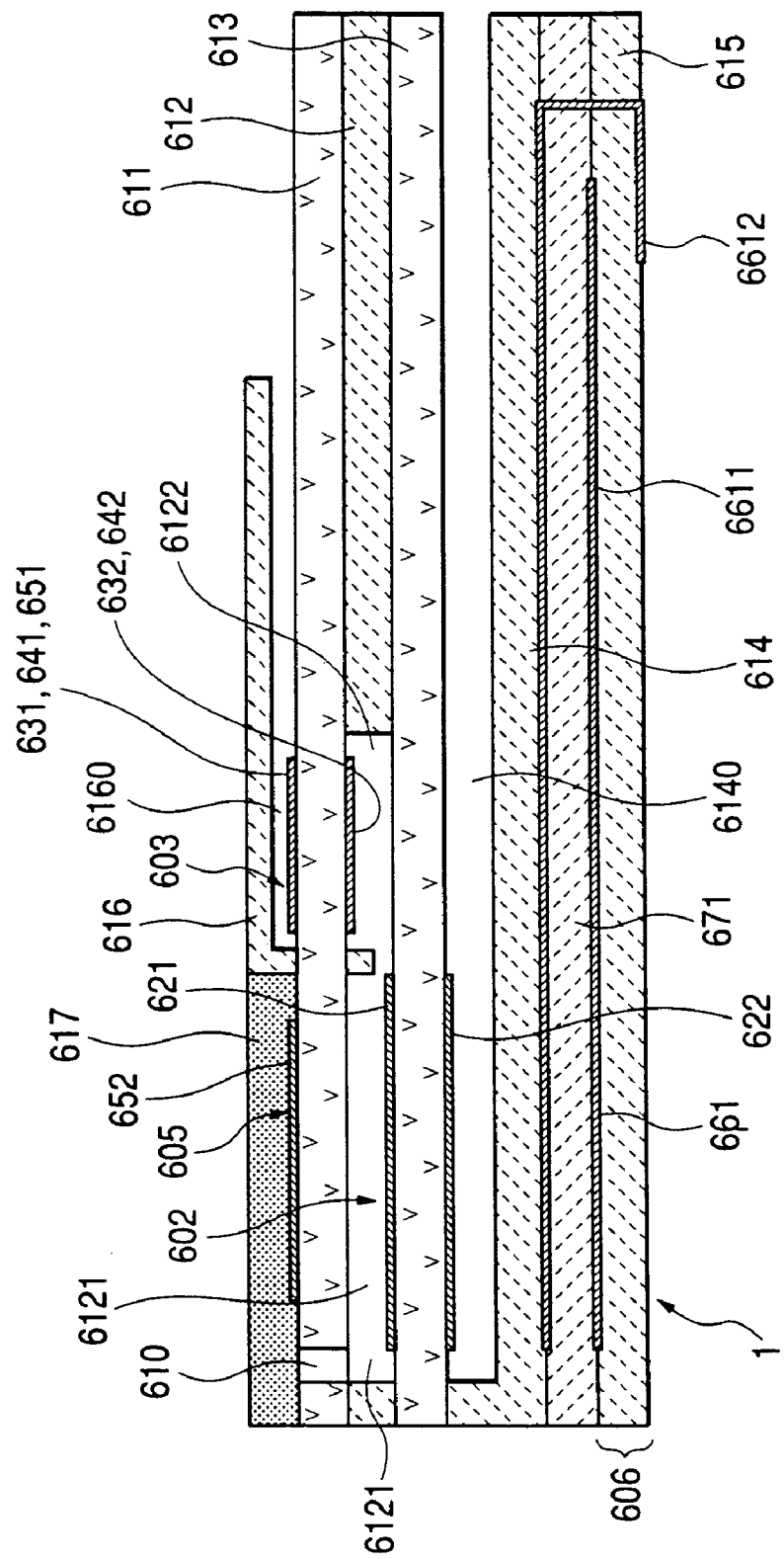
FIG. 23 is a longitudinal cross-sectional view showing a gas sensing element according to the seventh embodiment in which a conductive layer is electrically connected through a conductive through hole to a terminal.

Incidentally, it is also possible that, as shown in FIG. 23, the aforesaid conductive layer 607 is electrically connected through a conductive through hole 672 to a terminal 6612 connected to the minus side of the heater circuit 665. In this case, the electric potential of the conductive layer 607 falls and, hence, the leakage current can flow more easily.

Eighth Embodiment

Figure 24:
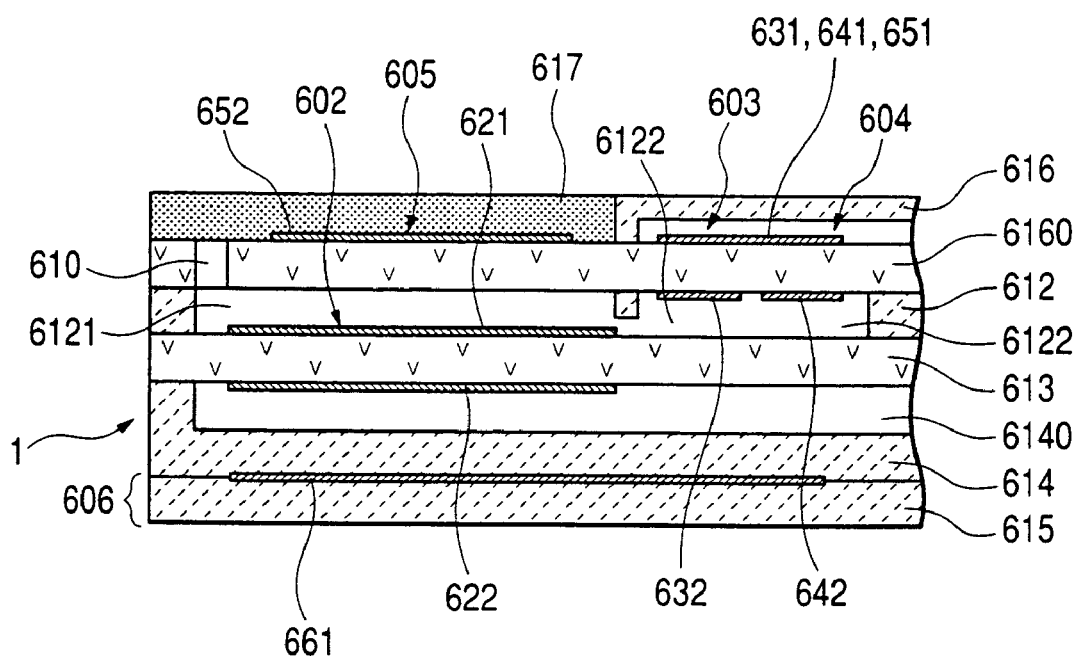
FIG. 24 is a cross-sectional view showing a gas sensing element according to an eighth embodiment of the present invention in which a monitor cell and a sensor cell are arranged in a longitudinal direction.

In a gas sensing element 1 according to an eighth embodiment of the present invention, the monitor cell 603 and the sensor cell 604 are disposed along the longitudinal direction of the gas sensing element 1 as shown in FIG. 24. The other construction is similar to that of the fifth embodiment. The effects of this embodiment are similar to those of the fifth embodiment.

Ninth Embodiment

Figure 25:
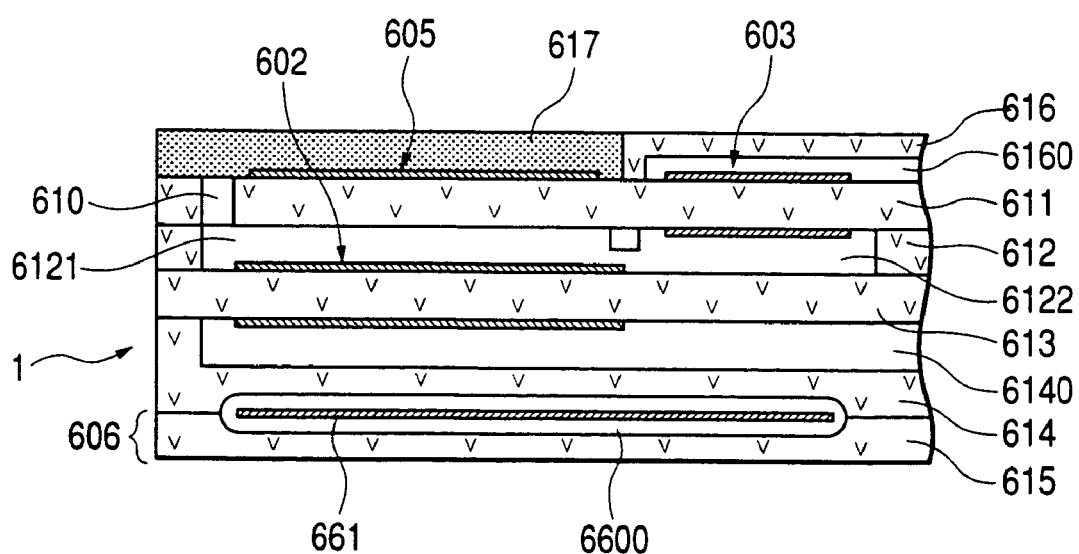
FIG. 25 is a cross-sectional view showing an essential part of a gas sensing element according to a ninth embodiment of the present invention in which a heat generator is covered with an insulating material.
Figure 26:
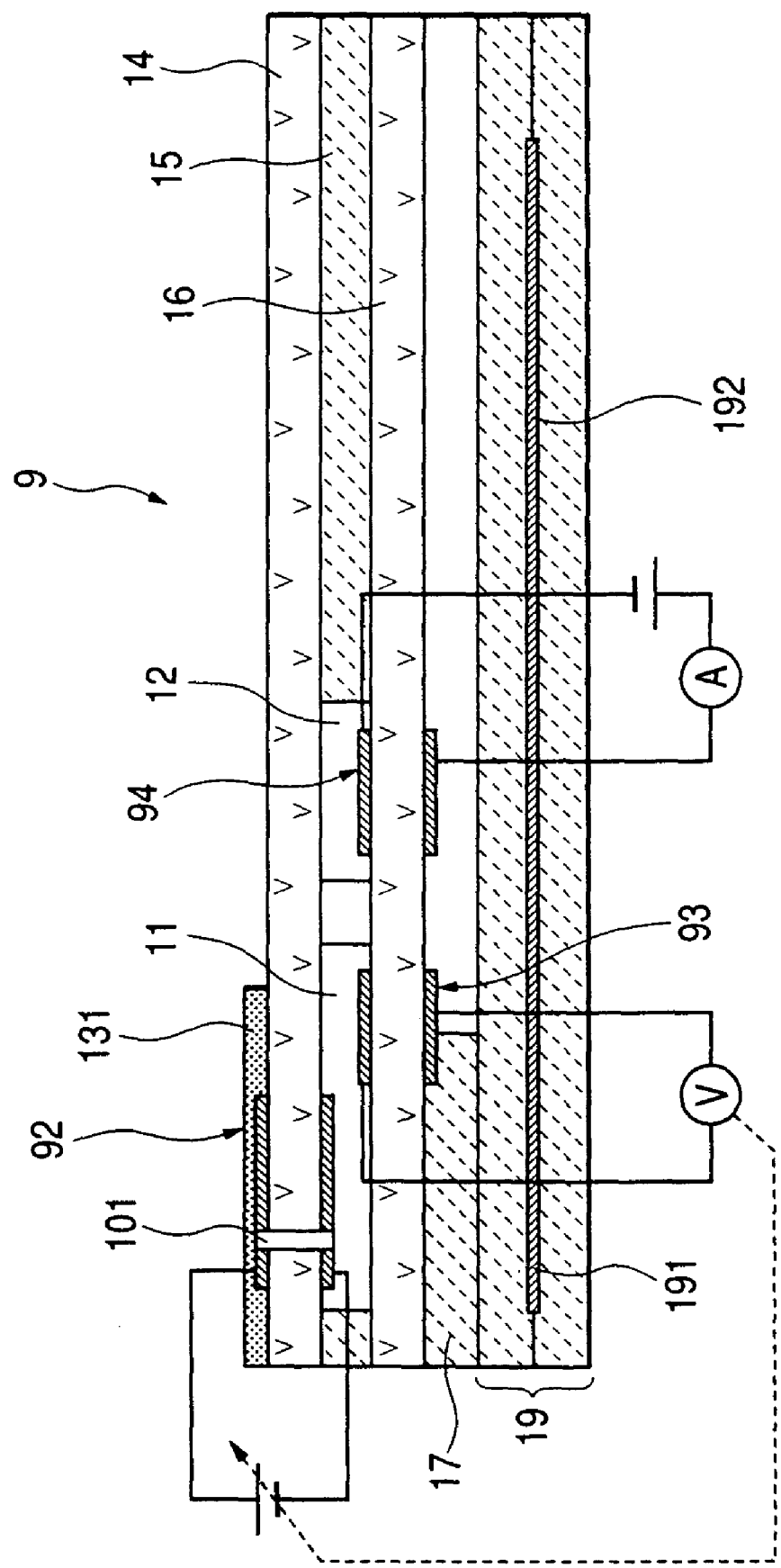
FIG. 26 is a longitudinal cross-sectional view showing a conventional multilayer gas sensing element.

Although a gas sensing element 1 according to a ninth embodiment of the present invention basically has the same construction as that of the gas sensing element 1 according to the fifth embodiment, the heater substrate 615 and the spacers 612, 614 and 616 are made of the same material as that of the solid electrolyte plates 611 and 613, and only the heat generator 661 is covered with (wrapped in) an insulating material 6600 as shown in FIG. 25.

In the case of this embodiment shown in FIG. 25, since the principal components of the gas sensing element 1 are made of the same material, when the gas sensing element 1 is produced in a manner such that a plurality of green sheets are built up and compressed and then calcined, calcination cracking, which stems from the difference in coefficient of thermal expansion between different kinds of materials, hardly occurs.

It should be understood that the present invention is not limited to the above-described embodiments, and that it is intended to cover all changes and modifications of the embodiments of the invention herein which do not constitute departures from the spirit and scope of the invention.

What is claimed is:

1. A gas sensing element comprising:
    a heater including:
    a heater substrate;
    a heat generator provided on said heater substrate for generating heat when energized; and
    a heater terminal electrically connected through a heater lead to said heat generator;
    a spacer for a measured gas chamber into which a measured gas is introduced from the external;
    a spacer for a reference gas chamber into which a reference gas is introduced;
    a solid electrolyte plate including an electrochemical cell having a pair of electrodes for detecting a specified gas concentration on the basis of a minute current stemming from oxygen ions and flowing between said pair of electrodes,
    with said heater, said spacers and said solid electrolyte plate being built up into a multilayer construction,
    wherein a leakage current conducting path is provided in the middle of an electrical path between said heater and said electrochemical cell for leading a leakage current from said heater to a portion other than said electrochemical cell; and
    a pump cell comprising a pump cell solid electrolyte plate and a pair of pump electrodes provided on said pump cell solid electrolyte plate for pumping oxygen with respect to said measured gas chamber, and
    wherein said pump cell solid electrolyte plate includes pump leads electrically connected to said pair of pump electrodes and said pump leads are electrically connected to terminals exposed to the exterior of said gas sensing element, with said leakage current conducting path being made through the use of said pump leads.

2. The element according to claim 1, wherein said heater, said reference gas chamber spacer, said pump cell solid electrolyte plate and said measured gas chamber spacer are built up in a state adjacent to each other, and one of said pump leads is located in a first boundary surface between one outer surface of said gas sensing element and an inner surface of said reference gas chamber and between said pump cell solid electrolyte plate and said reference gas chamber spacer, while the other pump lead is located in a second boundary surface between the other outer surface of said gas sensing element and an inner surface of said measured gas chamber and between said pump cell solid electrolyte plate and said measured gas chamber spacer.

3. The element according to claim 2, wherein, when a minimum width of said first boundary surface along a cross direction perpendicular to a longitudinal direction of said gas sensing element is taken to be A, a maximum width of said pump lead located in said first boundary surface along said cross direction is taken as a, a minimum width of said second boundary surface along said cross direction is taken as C and a maximum width of said pump lead located at said second boundary surface along said cross direction is taken as c, the widths are determined so that $0.1 \leq a/A$, $0.1 \leq c/C$.

4. The element according to claim 1, wherein said leakage current conducting path is made of one of a material containing at least a noble metal and a cermet containing a noble metal and ceramics.

5. A gas sensing element comprising:
    a heater including:
    a heater substrate;
    a heat generator provided on said heater substrate for generating heat when energized; and
    a heater terminal electrically connected through a heater lead to said heat generator;
    a spacer for a measured gas chamber into which a measured gas is introduced from the external;
    a spacer for a reference gas chamber into which a reference gas is introduced;
    a solid electrolyte plate including an electrochemical cell having a pair of electrodes for detecting a specified gas concentration on the basis of a minute current stemming from oxygen ions and flowing between said pair of electrodes,
    with said heater, said spacers and said solid electrolyte plate being built up into a multilayer construction,
    wherein a leakage current conducting path is provided in the middle of an electrical path between said heater and said electrochemical cell for leading a leakage current from said heater to a portion other than said electrochemical cell; and
    a pump cell including a pump cell solid electrolyte plate and a pair of pump electrodes provided on said pump cell solid electrolyte plate for pumping oxygen with respect to said measured gas chamber, and
    wherein said pump electrodes are made to cover an electrode projection plane formed by projecting a pair of electrodes for said electrochemical cell onto said pump cell solid electrolyte plate, and said leakage current conducting path is made through the use of said pump electrodes.

* * * * *